US011235162B2

(12) United States Patent
Reinke et al.

(10) Patent No.: US 11,235,162 B2
(45) Date of Patent: Feb. 1, 2022

(54) TISSUE CONDUCTION COMMUNICATION BETWEEN DEVICES

(71) Applicant: Medtronic, Inc., Minneapolis, MN (US)

(72) Inventors: James D. Reinke, Maple Grove, MN (US); Joel B. Artmann, Elk River, MN (US); Michael T. Hemming, Kiowa, CO (US); David J. Peichel, Minneapolis, MN (US); Jonathan P. Roberts, Coon Rapids, MN (US); Michael B. Terry, Camas, WA (US); Eric R. Williams, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 269 days.

(21) Appl. No.: 16/204,505

(22) Filed: Nov. 29, 2018

(65) Prior Publication Data
US 2019/0160293 A1    May 30, 2019

Related U.S. Application Data

(60) Provisional application No. 62/591,810, filed on Nov. 29, 2017.

(51) Int. Cl.
*A61N 1/372* (2006.01)
*A61N 1/375* (2006.01)
(Continued)

(52) U.S. Cl.
CPC ......... *A61N 1/37217* (2013.01); *A61N 1/365* (2013.01); *A61N 1/3756* (2013.01);
(Continued)

(58) Field of Classification Search
CPC .... A61N 1/37288; A61N 1/3656; A61N 1/05; A61N 1/3756; A61N 1/3956
See application file for complete search history.

(56) References Cited

U.S. PATENT DOCUMENTS

| 4,987,897 A | 1/1991 | Funke |
| 5,591,214 A | 1/1997 | Lu |

(Continued)

FOREIGN PATENT DOCUMENTS

EP    2385636    11/2011

OTHER PUBLICATIONS

Zhao et al., "Device, System and Method With Adaptive Timing for Tissue Conduction Communication Transmission ", U.S. Appl. No. 16/220,093, filed Dec. 14, 2018, 65 pages.

(Continued)

*Primary Examiner* — Gary Jackson
*Assistant Examiner* — Zahed Kabir

(57) ABSTRACT

A system, such as an IMD system, includes a tissue conductance communication (TCC) transmitter configured to generate a beacon signal by generating a carrier signal and modulating a first property of the carrier signal according to a first type of modulation. The TCC transmitter is configured to generate a data signal subsequent to the beacon signal by generating the carrier signal and modulating a second property of the carrier signal different than the first property according to a second type of modulation different than the first type of modulation.

23 Claims, 11 Drawing Sheets

(51) Int. Cl.
  *A61N 1/39* (2006.01)
  *A61N 1/365* (2006.01)
  *A61N 1/05* (2006.01)

(52) U.S. Cl.
  CPC ....... *A61N 1/37288* (2013.01); *A61N 1/3956* (2013.01); *A61N 1/3962* (2013.01); *A61N 1/05* (2013.01); *A61N 1/37264* (2013.01); *A61N 1/3975* (2013.01)

(56) References Cited

U.S. PATENT DOCUMENTS

| | | | |
|---|---|---|---|
| 6,076,016 | A | 6/2000 | Feierbach |
| 6,115,636 | A | 9/2000 | Ryan |
| 7,542,800 | B2 | 6/2009 | Libbus et al. |
| 7,623,930 | B2 | 11/2009 | Zeijlemaker et al. |
| 7,912,537 | B2 | 3/2011 | Lee et al. |
| 8,041,418 | B2 | 10/2011 | Giftakis et al. |
| 8,055,345 | B2 * | 11/2011 | Li .................... A61N 1/025 607/32 |
| 8,275,444 | B2 | 9/2012 | Zeijlemaker et al. |
| 8,412,352 | B2 | 4/2013 | Griswold et al. |
| 8,457,742 | B2 | 6/2013 | Jacobson |
| 8,720,276 | B2 | 5/2014 | Kuhn et al. |
| 8,738,126 | B2 | 5/2014 | Craig |
| 8,744,572 | B1 | 6/2014 | Greenhut et al. |
| 8,924,008 | B2 | 12/2014 | Yuyama et al. |
| 8,954,008 | B2 | 2/2015 | Wang et al. |
| 8,996,115 | B2 | 3/2015 | Trier et al. |
| 9,168,383 | B2 | 10/2015 | Jacobson et al. |
| 9,636,511 | B2 | 5/2017 | Carney et al. |
| 9,687,659 | B2 | 6/2017 | Von Arx et al. |
| 9,713,434 | B2 | 7/2017 | Barak |
| 2004/0011366 | A1 | 1/2004 | Schulman et al. |
| 2007/0239051 | A1 * | 10/2007 | Ghanem ............ A61B 5/4836 600/512 |
| 2009/0135886 | A1 | 5/2009 | Robertson et al. |
| 2011/0274432 | A1 * | 11/2011 | Cunningham ....... H04B 10/112 398/96 |
| 2012/0109258 | A1 | 5/2012 | Cinbis et al. |
| 2012/0277600 | A1 | 11/2012 | Greenhut |
| 2012/0323099 | A1 | 12/2012 | Mothilal et al. |
| 2013/0253345 | A1 | 9/2013 | Griswold et al. |
| 2013/0324825 | A1 | 12/2013 | Ostroff et al. |
| 2014/0011469 | A1 | 1/2014 | Fenn et al. |
| 2015/0057721 | A1 | 2/2015 | Stahmann et al. |
| 2015/0306375 | A1 | 10/2015 | Marshall et al. |
| 2015/0306410 | A1 | 10/2015 | Marshall et al. |
| 2016/0156388 | A1 * | 6/2016 | Zeine .................. H04W 76/14 307/104 |
| 2016/0213937 | A1 | 7/2016 | Reinke et al. |
| 2016/0213939 | A1 * | 7/2016 | Carney ............... A61N 1/3975 |
| 2016/0296760 | A1 | 10/2016 | Sahabi et al. |
| 2017/0173346 | A1 | 6/2017 | Kane et al. |

OTHER PUBLICATIONS

Roberts et al., "Signal Transmission Optimization for Tissue Conduction Communication", U.S. Appl. No. 16/202,418, filed Nov. 28, 2018, 82 pages.

Peichel et al., "Implantable Medical Device and Method To Minimize Artifact From Tissue Conduction Communication Transmission", U.S. Appl. No. 62/591,806, filed Nov. 29, 2017, 76 pages.

Peichel et al., "Tissue Conduction Communication in an Implantable Medical Device System", U.S. Appl. No. 62/591,813, filed Nov. 29, 2017, 93 pages.

(PCT/US2018/063057) PCT Notification of Transmittal of the International Search Report and the Written Opinion of the International Searching Authority, dated Feb. 11, 2019, 14 pages.

* cited by examiner

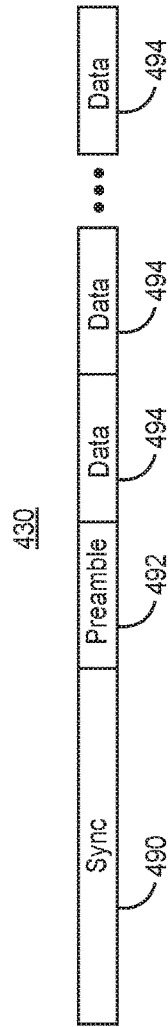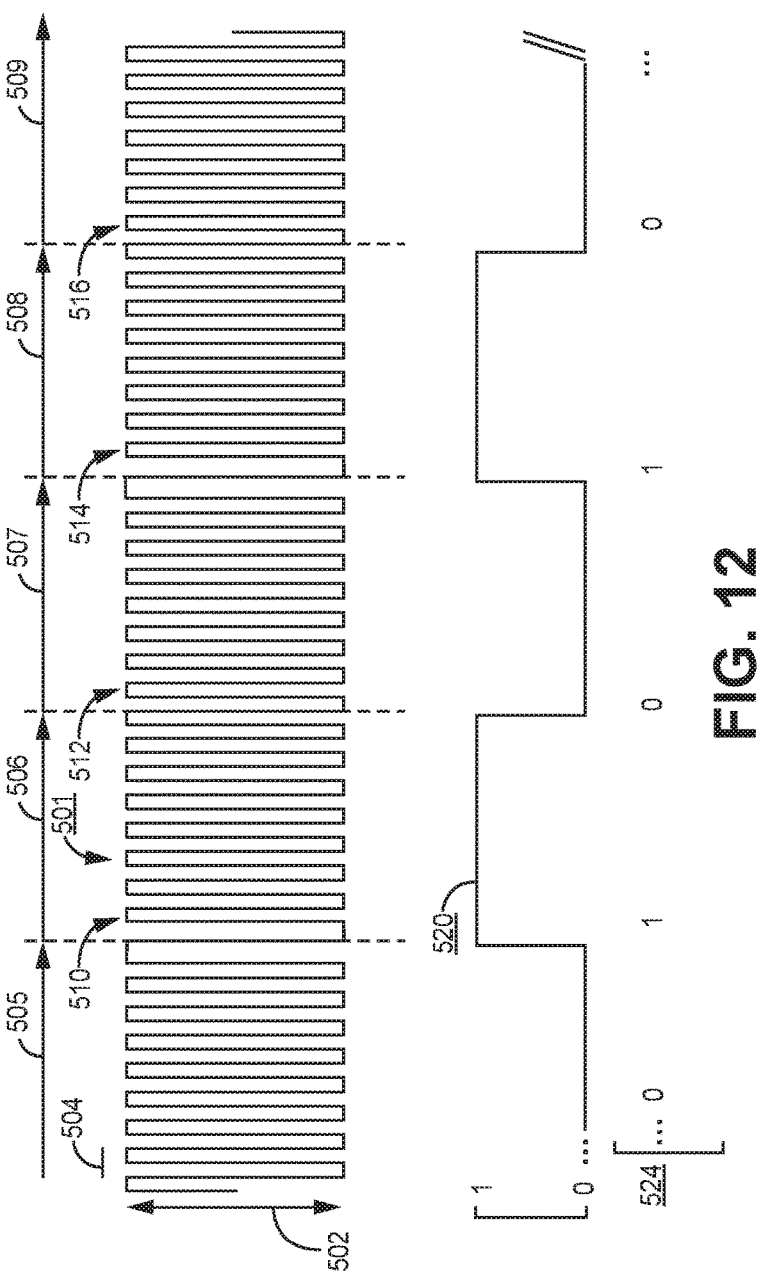

TISSUE CONDUCTION COMMUNICATION BETWEEN DEVICES

TECHNICAL FIELD

The disclosure relates generally to devices, systems and methods for communicating between devices using tissue conduction communication.

BACKGROUND

Communication between two or more devices associated with a person, e.g., implanted within the person and/or attached to or otherwise contacting the person, may be desirable in a number of applications, such as for monitoring or managing health of a patient. Communication between these devices may, for example, enable the exchange of information, coordinated monitoring of a health condition and/or coordinated therapy to treat health conditions. Such systems, some examples of which are described below, may communicate using tissue conduction communication (TCC). TCC uses the human body as the medium of communication. TCC may sometimes be referred to as human body conduction (HBC) or intrabody communication.

A wide variety of implantable medical devices (IMDs) for delivering a therapy to or monitoring a physiological condition of a patient have been used clinically or proposed for clinical use in patients. Examples include IMDs that deliver therapy to and/or monitor conditions associated with the heart, muscle, nerve, brain, stomach or other tissue. Some therapies include the delivery of electrical stimulation to such tissues. Some IMDs may employ electrodes for the delivery of therapeutic electrical signals to such organs or tissues, electrodes for sensing intrinsic physiological electrical signals within the patient, which may be propagated by such organs or tissue, and/or other sensors for sensing physiological signals of a patient.

Implantable cardioverter defibrillators (ICDs), for example, may be used to deliver high energy defibrillation and/or cardioversion shocks to a patient's heart when atrial or ventricular tachyarrhythmia, e.g., tachycardia or fibrillation, is detected. An ICD may detect a tachyarrhythmia based on an analysis of a cardiac electrogram sensed via electrodes, and may deliver anti-tachyarrhythmia shocks, e.g., defibrillation shocks and/or cardioversion shocks, via electrodes. An ICD or an implantable cardiac pacemaker, as another example, may provide cardiac pacing therapy to the heart when the natural pacemaker and/or conduction system of the heart fails to provide synchronized atrial and ventricular contractions at rates and intervals sufficient to sustain healthy patient function. ICDs and cardiac pacemakers may also provide overdrive cardiac pacing, referred to as anti-tachycardia pacing (ATP), to suppress or convert detected tachyarrhythmias in an effort to avoid cardioversion/defibrillation shocks.

Some IMDs are coupled to one or more of the electrodes used to sense electrical physiological signals and deliver electrical stimulation via one or more leads. A medical electrical lead carrying sensing and/or electrical therapy delivery electrodes allow the IMD housing to be positioned a location spaced apart from the target site for sensing and/or stimulation delivery. For example, a subcutaneously or sub-muscularly implanted housing of an ICD or implantable cardiac pacemaker may be coupled to endocardial electrodes via one or more medical electrical leads that extend transvenously to the patient's heart. Other ICD systems, referred to as extracardiovascular ICD systems, are not coupled to any transvenous leads, and instead sense and deliver shocks via electrodes implanted away from the patient's heart, e.g., implanted subcutaneously or substernally. The extra-cardiovascular electrodes may be provided along the housing of the subcutaneous ICD and/or coupled to the housing via one or more leads extending subcutaneously, submuscularly or substernally from the housing.

Leadless IMDs may also be used to deliver therapy to a patient, and/or sense physiological parameters of a patient. In some examples, a leadless IMD may include one or more electrodes on its outer housing to deliver therapeutic electrical stimulation to the patient, and/or sense intrinsic electrical signals of patient. For example, a leadless pacemaker may be used to sense intrinsic depolarizations or other physiological parameters of the patient, and/or deliver therapeutic electrical stimulation to the heart. A leadless pacemaker may be positioned within or outside of the heart and, in some examples, may be anchored to a wall of the heart via a fixation mechanism.

In some situations, two or more IMDs are implanted within a single patient. It may be desirable for the two or more IMDs to be able to communicate with each other, e.g., to coordinate, or cooperatively provide, sensing for monitoring the patient and/or therapy delivery. Although some IMDs communicate with other medical devices, e.g., with external programming devices, using radio-frequency (RF) telemetry, TCC allows for communication between two or more IMDs by transmitting signals between the electrodes of two IMDs via a conductive tissue pathway. Likewise, TCC may be utilized to communicate between an IMD and an external device having electrodes proximate to or in contact with the skin of the patient or between two external devices having electrodes proximate to or in contact with the skin of the patient.

SUMMARY

The techniques of this disclosure generally relate to a device, system and methods for transmitting and receiving TCC signals. The techniques of this disclosure are described in the context of an IMD. However, the techniques can be utilized by any device, medical or non-medical, implanted or external, that communicates using TCC. A TCC transmitter included in an IMD is configured to generate a carrier signal and modulate the carrier signal to generate a beacon signal during a wakeup mode of the TCC transmitter and modulate the carrier signal to generate a data signal during a data transmission mode of the TCC transmitter. Among other TCC transmission techniques disclosed herein, the TCC transmitter is capable of generating and transmitting a modulated beacon signal according to a first type of modulation and one or more data packets according to a second, different type of modulation. The receiving device of the IMD system includes a TCC signal detector configured to detect the beacon signal based on the first modulation type then wake up for receiving and demodulating data packets modulated according to the second type of modulation.

In one example, the disclosure provides an IMD configured to transmit a TCC signal. The IMD includes a housing and a TCC transmitter enclosed by the housing. The TCC transmitter includes a controller, a drive signal circuit, and a polarity switching circuit for generating TCC signals transmitted to a receiving device via a transmitting electrode vector coupleable to the IMD. The controller is configured to control the TCC transmitter to generate a beacon signal by generating a carrier signal and modulating a first property of the carrier signal according to a first type of modulation, and generate a data signal subsequent to the beacon signal by generating the carrier signal and modulating a second property of the carrier signal different than the first property according to a second type of modulation different than the first type of modulation.

In another example, the disclosure provides a method for transmitting a tissue conduction communication (TCC) signal by an implantable medical device (IMD) having a TCC transmitter. The method includes generating a beacon signal by the TCC transmitter by generating a carrier signal and modulating a first property of the carrier signal according to a first type of modulation and generating a data signal subsequent to the beacon signal by generating the carrier signal and modulating a second property of the carrier signal different than the first property according to a second type of modulation different than the first type of modulation.

In another example, the disclosure provides a non-transitory, computer-readable storage medium comprising a set of instructions which, when executed by a controller of IMD having a TCC transmitter, cause the TCC transmitter to generate a beacon signal by generating a carrier signal and modulating a first property of the carrier signal according to a first type of modulation and generate a data signal subsequent to the beacon signal by generating the carrier signal and modulating a second property of the carrier signal different than the first property according to a second type of modulation different than the first type of modulation.

In yet another example, the disclosure provides IMD configured to receive a TCC signal. The IMD includes a housing and a TCC signal detector enclosed by the housing. The TCC signal detector is configured to detect a beacon signal transmitted from a transmitting device by detecting a first type of modulation of a first property of a carrier signal and detect a data signal transmitted by the transmitting device subsequent to the beacon signal by detecting a second type of modulation of a second property of the carrier signal different than the first property. The second type of modulation is different than the first type of modulation.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 11 is a diagram of a data packet that may be transmitted during a data transmission mode of the TCC transmitter.

FIG. 12 is a conceptual diagram of a portion of one data byte that may be included in the data packet of FIG. 11.

DETAILED DESCRIPTION

Wireless communication between two or more medical devices may be desired for a number of reasons, including to exchange data and/or to coordinate, or cooperatively provide, sensing of physiological signals and/or therapy delivery. TCC signals may be wirelessly transmitted from one IMD to one or more IMDs co-implanted within a patient and/or to an external medical device having skin or surface electrodes coupled to the patient for transmitting and/or receiving TCC signals. Some IMDs and external medical devices may be configured to sense an electrophysiological signal via sensing electrodes and/or monitor electrical impedance such as transthoracic impedance signals. Examples of electrophysiological signals include a cardiac electrical signal produced by the patient's heart, an electromyogram signal produced by skeletal muscle tissue, and other electrophysiological signals produced by the brain, nerve or muscle tissue. Transmission of a communication signal may cause interference with electrical signal sensing circuitry. Transmission of a communication signal through body tissue may unintentionally cause electrical stimulation of muscle or nerves depending on the amplitude and frequency of the transmitted signal.

An IMD or an external medical device that includes electrical signal sensing circuitry configured to receive an electrophysiological signal or monitor impedance may be a TCC transmitting device, an intended TCC receiving device, or an unintended receiving device that is coupled to electrodes within the tissue conduction pathway of a TCC signal being transmitted between two other devices. In each case, a transmitted TCC signal may be received by sensing electrodes coupled to the transmitting or receiving IMD or external device and interfere with the sensing circuitry. In other examples, a transmitting or receiving device may be configured to monitor the electrical impedance of one or more medical electrical leads or the tissue impedance between one or more electrode vectors coupled to the device. TCC techniques are disclosed herein for enabling reliable communication of multi-byte streams of encoded data between medical devices while minimizing the likelihood of a TCC signal causing unintended stimulation and interfering with electrophysiological signal sensing circuitry, impedance monitoring, or other monitoring of electrical signals performed by an IMD system.

Figure 1:
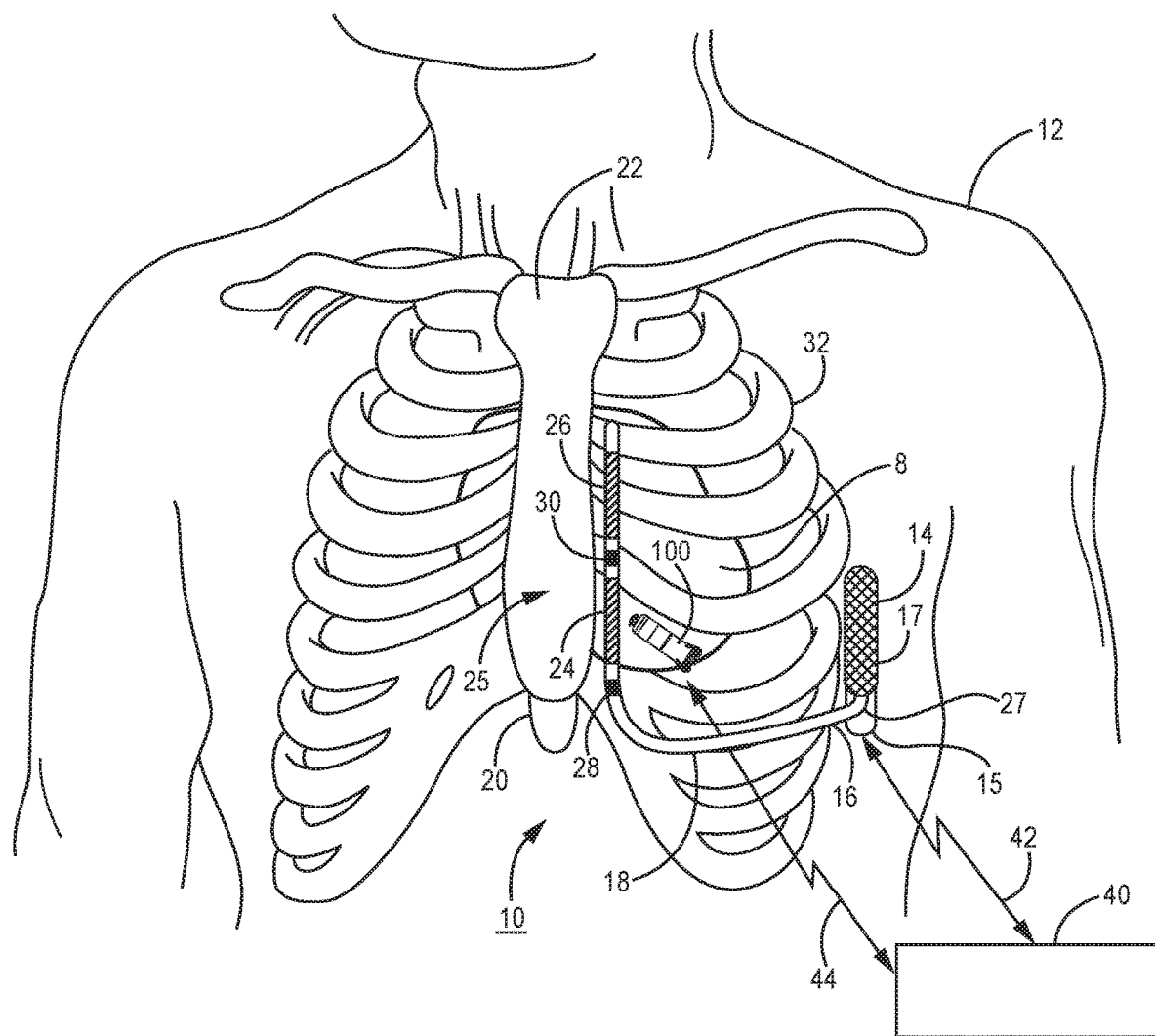
FIG. 1 is a conceptual diagram of an IMD system capable of TCC according to one example.

FIG. 1 is a conceptual diagram of an IMD system 10 capable of TCC according to one example. FIG. 1 is a front view of a patient 12 implanted with IMD system 10. IMD system 10 includes an ICD 14, an extra-cardiovascular electrical stimulation and sensing lead 16 coupled to ICD 14, and an intra-cardiac pacemaker 100. ICD 14 and pacemaker 100 may be enabled to communicate via TCC for transmitting a variety of data or commands. For example, ICD 14 and pacemaker 100 may be configured to communicate via TCC to confirm detected cardiac events or a detected heart rhythm and/or coordinate delivery of cardiac pacing pulses for bradycardia pacing, ATP therapy, cardioversion/defibrillation (CV/DF) shocks, post-shock pacing, cardiac resynchronization therapy (CRT) or other electrical stimulation therapies in response to an abnormal heart rhythm being detected by one or both of the IMDs 14 and 100.

IMD system 10 senses cardiac electrical signals, such as R-waves attendant to ventricular depolarizations and/or P-waves attendant to an atrial depolarizations, for detecting abnormal heart rhythms with high sensitivity and specificity to enable IMD system 10 to deliver (or withhold) appropriate therapies at appropriate times. Transmission of TCC signals by an IMD, e.g., by ICD 14 or pacemaker 100, may cause interference with the sensing circuitry of the transmitting IMD, resulting in false sensing of a cardiac event. Such false sensing of cardiac events due to TCC interference with a cardiac event detector included in electrical signal sensing circuitry may lead to withholding a pacing pulse when a pacing pulse is actually needed or contribute to false detection of a tachyarrhythmia event. The TCC signal transmission techniques disclosed herein reduce the likelihood of a TCC signal being falsely detected as a cardiac event by a cardiac electrical signal sensing circuit of the transmitting device.

The TCC signal transmission techniques may also reduce the likelihood that another IMD implanted in patient 12 that is configured to sense electrophysiological signals, such as R-waves and/or P-waves, falsely senses TCC signals as physiological signals. Another IMD implanted in patient 12 may be the intended receiving device of the transmitted TCC signals, e.g., pacemaker 100 receiving signals from ICD 14 or vice versa. In other cases, another IMD co-implanted in patient 12 may not be the receiving device of transmitted TCC signals but may be configured to sense electrophysiological signals via electrodes coupled to the co-implanted IMD. A voltage signal may develop across sensing electrodes of the intended or unintended receiving device and interfere with electrophysiological sensing and event detection. The TCC signal transmission techniques of the present disclosure may reduce or eliminate the incidence of TCC signals being sensed as electrophysiological signals or events by any other IMD implanted in patient 12 or an external device having electrodes coupled to the patient externally.

FIG. 1 is described in the context of an IMD system 10 including ICD 14 and pacemaker 100 capable of sensing cardiac electrical signals produced by the patient's heart 8 and delivering cardioversion and/or defibrillation (CV/DF) shocks and cardiac pacing pulses to the patient's heart 8. In some examples, the TCC communication may be "one-way" communication, e.g., from ICD 14 to pacemaker 100 or from pacemaker 100 to ICD 14. In other examples, the TCC communication may be "two-way" communication between ICD 14 and pacemaker 100. It is recognized that aspects of the TCC signal transmission techniques disclosed herein may be implemented in a variety of IMD systems which may include an ICD, pacemaker, cardiac monitor or other sensing-only device, neurostimulator, drug delivery device or other implantable medical device(s). The TCC signal transmission techniques disclosed herein may be implemented in any IMD system that requires communication between one IMD and at least one other medical device, implanted or external. Moreover, the techniques described herein may be utilized by two external devices that communicate using TCC. The techniques may also have non-medical applications as well for devices that are implanted and/or external and communicate using TCC.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). In other instances, the housing 15 of ICD 14 may include a plurality of electrodes on an outer portion of the housing. The outer portion(s) of the housing 15 functioning as an electrode(s) may be coated with a material, such as titanium nitride for reducing post-stimulation polarization artifact. Housing 15 may be used as an active can electrode for use in delivering CV/DF shocks or other high voltage pulses delivered using a high voltage therapy circuit. In other examples, housing 15 may be available for use in delivering relatively lower voltage cardiac pacing pulses and/or for sensing cardiac electrical signals in combination with electrodes carried by lead 16. In any of these examples, housing 15 may be used in a transmitting electrode vector for transmitting TCC signals according to the techniques disclosed herein.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, TCC transmitting and receiving circuitry, power sources and other components for sensing cardiac electrical signals, detecting a heart rhythm, and controlling and delivering electrical stimulation pulses to treat an abnormal heart rhythm and for transmitting TCC signals to pacemaker 100 and/or receiving TCC signals from pacemaker 100.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIG. 1, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be selectively activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality, and/or TCC signal transmission and receiving in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect and discriminate tachyarrhythmias. Electrodes 24 and 26 may be used in a TCC signal transmitting electrode vector in combination with each other, collectively with housing 15, or individually with housing 15. In the case of ICD 14 being configured to receive TCC signals from pacemaker 100, electrodes 24, 26 and/or housing 15 may be used in a TCC receiving electrode vector. The transmitting and receiving electrode vectors may be the same or different vectors.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., delivery of relatively low voltage pacing pulses and/or sensing of cardiac electrical signals, as opposed to delivering high voltage cardioversion defibrillation shocks. In some instances, electrodes 28 and 30 may provide only pacing functionality, only sensing functionality or both. Furthermore, one or both of electrodes 28 and 30 may be used in TCC signal transmission and/or receiving in some examples.

ICD 14 may obtain cardiac electrical signals corresponding to electrical activity of heart 8 via a combination of sensing electrode vectors that include combinations of electrodes 24, 26, 28, 30 and/or housing 15. Various sensing electrode vectors utilizing combinations of electrodes 24, 26, 28, and 30 may be selected by sensing circuitry included in ICD 14 for receiving a cardiac electrical signal via one or more sensing electrode vectors.

In the example illustrated in FIG. 1, electrode 28 is located proximal to defibrillation electrode 24, and electrode 30 is located between defibrillation electrodes 24 and 26. Electrodes 28 and 30 may be ring electrodes, short coil electrodes, hemispherical electrodes, or the like. Electrodes 28 and 30 may be positioned at other locations along lead body 18 and are not limited to the positions shown. In other examples, lead 16 may include none, one or more pace/sense electrodes and/or one or more defibrillation electrodes.

A TCC transmitting electrode vector may be selected from defibrillation electrodes 24, 26 and housing 15 for transmitting TCC signals produced by a TCC transmitter included in ICD 14. Electrodes, such as defibrillation electrodes 24 and 26 and housing 15, having a relatively large surface area may be used to transmit TCC signals to reduce the impedance of the transmitting electrode vector. A low impedance of the transmitting electrode vector maximizes the injected current signal.

The TCC transmitting electrode vector may be selected to both reduce impedance of the transmitting electrode vector and maximize transimpedance from the transmitting electrode vector to the intended receiving electrode pair. As used herein, the term "transimpedance" refers to the voltage received at a TCC signal receiving electrode vector divided by the transmitted current (voltage out divided by current in). As such, the transimpedance for a given TCC communication electrode vector for each of two IMDs configured to communicate bidirectionally is the same for communication in both directions for a given set of transmitting and receiving electrode vectors. By maximizing transimpedance, the voltage signal at the intended receiving electrodes is maximized for a given current signal injected into the tissue conductance pathway. As such, a low impedance of the transmitting electrode vector and high transimpedance of the TCC pathway increases the received TCC signal strength (voltage signal) at the receiving electrode vector.

Among the factors that may contribute to a maximized transimpedance of the TCC pathway are a substantially parallel electrical configuration of the transmitting and receiving electrode vectors, relatively wide spacing of the transmitting electrodes, relatively wide spacing of the receiving electrodes, and close proximity of the transmitting electrode vector to the receiving electrode vector. A transmitting electrode vector closer in proximity to the receiving electrode vector improves the strength of the TCC signal compared to a larger separation of the transmitting and receiving electrode vectors. The optimal orientation for the receiving electrode vector is parallel to the conductive tissue pathway of the current flow. A transmitting electrode vector that is substantially electrically parallel to the receiving electrode vector improves the strength of the TCC signal compared to the receiving electrode vector being orthogonal to the pathway of the current flow through the body tissue, which may result in a null signal.

A parallel electrical configuration between the transmitting and receiving electrode vectors may coincide with physically parallel electrode pairs. The physical electrode vectors may be viewed in some cases as the line the extends from one electrode of the vector to the other electrode of the vector to determine orientation of the transmitting and received vectors relative to one another. In some instances, however, physically parallel electrode pairs may not be electrically parallel depending on the electrical conduction properties of the intervening tissues. For example, a body tissue having relatively low electrical conductance, such as lung tissue, compared to other surrounding tissues, may require a physical electrode configuration that is not necessarily parallel in order to achieve an electrical configuration that is substantially parallel.

The TCC transmitting electrode vector may be selected to include electrodes that are not coupled to ICD sensing circuitry, e.g., a cardiac event detector configured to sense R-waves and/or P-waves from an electrical signal received by a sensing electrode vector. Use of an electrode for TCC signal transmission that is also coupled to a cardiac electrical event detector or other electrical signal sensing circuitry may increase interference with cardiac event detection or other electrical signal monitoring. The transmitting electrode vector may be selected to include at least one or both electrodes that are not coupled to the cardiac electrical event detector of ICD 14 so that TCC signals that are unintentionally received by the cardiac event detector are received via a transimpedance pathway from the transmitting electrode vector to the sensing electrode vector rather than directly through the sensing electrode impedance.

In other examples, however, the TCC transmitting electrode vector may include one or more electrodes coupled to cardiac electrical event detector included in ICD 14. A transmitting electrode vector may include electrodes coupled to the ICD sensing circuitry when the resulting transmitting electrode vector is optimal in other ways, e.g., low impedance and high transimpedance. Transmission of TCC signals using one or both electrodes included in a sensing electrode vector coupled to a cardiac event detector may be selected in a trade-off for optimizing other considerations in achieving reliable TCC signal transmission and reception. TCC signal transmission techniques disclosed herein may reduce or eliminate interference of the TCC signal transmission with cardiac event (or other electrophysiological signal) sensing as well as other sensing functions such as electrical impedance monitoring of a medical electrical lead or body tissue.

In one example, defibrillation electrode 24 may be selected in combination with housing 15 for transmitting TCC signals to pacemaker 100. In other examples, TCC signals may be transmitted by ICD 14 using defibrillation electrode 26 and housing 15 or using two defibrillation electrodes 24 and 26. The transmitting electrode vector impedance (delivered voltage divided by delivered current) may be up to hundreds of ohms. The transimpedance of the TCC pathway that includes a transmitting electrode vector including one defibrillation electrode 24 or 26 paired with housing 15 may be less than 10 ohms and even less than 1 ohm. A high transimpedance at the TCC signal transmission frequency is desired to produce a relatively high voltage on the receiving electrodes for a given injected current of the TCC signal.

The electrode pair selected for transmitting TCC signals may include one or both of pace/sense electrodes 28 and 30 in some examples. For example, the pace/sense electrode 28 or 30 may be paired with housing 15, defibrillation electrode 24 or defibrillation electrode 26 for transmitting TCC signals. The impedance of the transmitting electrode vector may be increased due to the relatively smaller surface area of pace/sense electrodes 28 and 30, which may have the effect of lowering the injected current during TCC signal transmission and thereby lowering the received voltage signal at the receiving electrode vector.

ICD 14 may be configured to select a TCC transmitting electrode vector from among multiple possible vectors using electrodes 24, 26, 28, 30 and housing 15 to achieve the best TCC signal strength at the receiving electrodes of pacemaker 100 and/or reduce TCC signal interference with cardiac event detection, impedance monitoring, or other functions performed by the ICD sensing circuit and/or by a sensing circuit of pacemaker 100. In some examples, multiple vectors may be used to transmit TCC signals to cover different angles in three-dimensional space to achieve at least one TCC transmitting vector that is substantially electrically parallel to the receiving electrode vector. The electrical configuration of a single transmitting vector relative to the TCC receiving vector may be time-varying due to heart motion when the receiving electrode vector is within or coupled to the patient's heart, as in the case of pacemaker 100.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum or substernally under the ribcage and/or sternum 22. Although illustrated in FIG. 1 as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous, submuscular or substernal paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry of ICD 14, such as a signal generator for therapy delivery and TCC signal transmission and/or a sensing circuit for sensing cardiac electrical signals and/or receiving TCC signals, via connections in the connector assembly 17, including associated electrical feedthroughs crossing housing 15.

The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14. The electrical conductors also transmit TCC signals from a TCC transmitter to electrodes selected for transmitting the TCC signals. In some examples, ICD 14 may receive TCC signals from pacemaker 100 in which case the TCC signals are conducted from a receiving pair of electrodes to a TCC signal receiver enclosed by housing 15.

The lead body 18 of lead 16 may be formed from a non-conductive material and shaped to form one or more lumens within which the one or more conductors extend. Lead body 18 may be a flexible lead body that conforms to an implant pathway. In other examples, lead body 18 may include one or more preformed curves. Various example configurations of extra-cardiovascular leads and electrodes and dimensions that may be implemented in conjunction with the TCC transmission techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 analyzes the cardiac electrical signals received from one or more sensing electrode vectors to monitor for abnormal rhythms, such as bradycardia, tachycardia or fibrillation. ICD 14 may analyze the heart rate and morphology of the cardiac electrical signals to monitor for tachyarrhythmia in accordance with any of a number of tachyarrhythmia detection techniques. ICD 14 generates and delivers electrical stimulation therapy in response to detecting a tachyarrhythmia, e.g., ventricular tachycardia (VT) or ventricular fibrillation (VF), using a therapy delivery electrode vector which may be selected from any of the available electrodes 24, 26, 28 30 and/or housing 15. ICD 14 may deliver ATP in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally.

Pacemaker 100 is shown as a leadless intracardiac pacemaker configured to receive TCC signals from ICD 14 via housing-based electrodes in the examples presented herein and may be configured to transmit TCC signals via housing-based electrodes to ICD 14. Pacemaker 100 may be delivered transvenously and anchored by a fixation member at an intracardiac pacing and sensing site. For example, pacemaker 100 may be implanted in an atrial or ventricular chamber of the patient's heart. In further examples, pacemaker 100 may be attached to an external surface of heart 8 (e.g., in contact with the epicardium) such that pacemaker 100 is disposed outside of heart 8.

Pacemaker 100 is configured to deliver cardiac pacing pulses via a pair of housing-based electrodes and may be configured to sense cardiac electrical signals for determining the need and timing of a delivered pacing pulse. For example, pacemaker 100 may deliver bradycardia pacing pulses, rate responsive pacing pulses, ATP, post-shock pacing pulses, CRT pacing pulses, and/or other pacing therapies. Pacemaker 100 may include a TCC receiver that receives and demodulates TCC signals transmitted from ICD 14 via housing-based electrodes. Pacemaker 100 may include a TCC transmitter that transmits TCC signals to ICD 14 via the housing-based electrodes. Pacemaker 100 is described in greater detail below in conjunction with FIG. 3. An example intracardiac pacemaker that may be included in an IMD system employing TCC is described in U.S. Pat. No. 8,744,572 (Greenhut et al.) incorporated herein by reference in its entirety.

In some examples, pacemaker 100 may be implanted in the right atrium, the right ventricle or the left ventricle of heart 8 to sense electrical activity of heart 8 and deliver pacing therapy. In other examples, system 10 may include two or more intracardiac pacemakers 100 within different chambers of heart 8 (e.g., within the right atrium, the right ventricle, and/or left ventricle). ICD 14 may be configured to transmit TCC signals to one or more pacemakers implanted within the patient's heart 8 to coordinate electrical stimulation therapy delivery. For example, ICD 14 may transmit command signals to cause pacemaker 100 to deliver a cardiac pacing pulse, ATP therapy, or request confirmation of sensed cardiac electrical events or a tachyarrhythmia detection.

An external device 40 is shown in telemetric communication with ICD 14 by a wireless communication link 42 and pacemaker 100 via a wireless communication link 44. External device 40 may include a processor, display, user interface, telemetry unit and other components for communicating with ICD 14 and pacemaker 100 for transmitting and receiving data via communication link 42 and 44, respectively. Communication link 42 or 44 may be established between ICD 14 or pacemaker 14, respectively, and external device 40 using a radio frequency (RF) link such as BLUETOOTH®, Wi-Fi, or Medical Implant Communication Service (MICS) or other RF or communication frequency bandwidth. In some examples, ICD 14 or pacemaker 100 may communicate with an external device 40 using TCC, e.g., using receiving surface electrodes coupled to external device 40 are placed externally on patient 12.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters) and therapy control parameters used by ICD 14. Data stored or acquired by ICD 14, including physiological signals or associated derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

In some examples, pacemaker 100 is not capable of bidirectional communication with external device 40. ICD 14 may operate as a control device and pacemaker 100 as a responder. Pacemaker 100 may receive TCC communication signals from ICD 14 that include operating control data and commands (which may be transmitted from external device 40 to ICD 14) so that RF telemetry circuitry need not be included in pacemaker 100. Pacemaker 100 may transmit data, such as information related to delivered pacing therapy and/or acquired cardiac electrical signals on command from ICD 14 via TCC transmissions, and ICD 14 may transmit data received from pacemaker 100 to external device 40 via RF communication.

Figure 2:
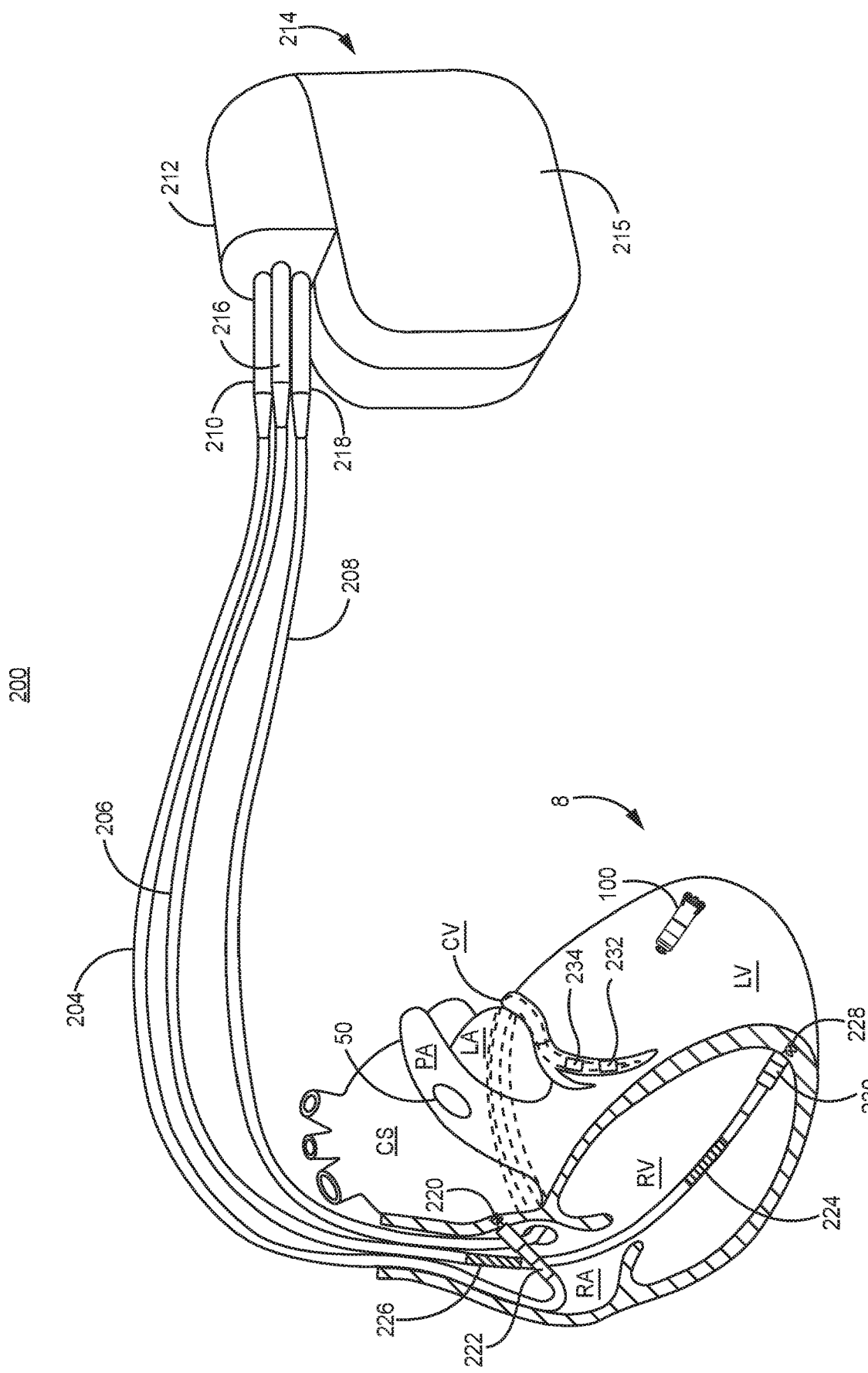
FIG. 2 is a conceptual diagram of an IMD system configured to communicate using TCC techniques disclosed herein according to another example.

FIG. 2 is a conceptual diagram of an IMD system 200 configured to communicate using TCC transmission techniques disclosed herein according to another example. The IMD system 200 of FIG. 2 includes an ICD 214 coupled to a patient's heart 8 via transvenous electrical leads 204, 206, and 208. IMD system 200 may include a leadless pacemaker 100 and/or a leadless sensor 50. Sensor 50 is shown as a leadless pressure sensor positioned in the pulmonary artery for monitoring pulmonary arterial pressure. Leadless pressure sensor 50, also referred to herein as "pressure sensor" 50, may be positioned at other intracardiac or arterial locations for monitoring blood pressure. In other examples, the IMD system 200 (or IMD system 10 of FIG. 1) may include other wireless sensors performing sensing-only or monitoring-only functions configured to send and/or receive TCC signals to/from ICD 214 (or ICD 14 of FIG. 1) and/or pacemaker 100. Other wireless sensors may include, for example, an electrocardiogram (ECG) monitor, an oxygen monitor, acoustical monitor, accelerometer, bioimpedance monitor, pH monitor, temperature monitor, insulin monitor, or other sensing device including one or any combination of sensors.

ICD 214 includes a connector block 212 that may be configured to receive the proximal ends of a right atrial (RA) lead 204, a right ventricular (RV) lead 206 and a coronary sinus (CS) lead 208, which are advanced transvenously for positioning electrodes for sensing and stimulation in three or all four heart chambers. RV lead 206 is positioned such that its distal end is in the right ventricle for sensing RV cardiac signals and delivering pacing or shocking pulses in the right ventricle. For these purposes, RV lead 206 is equipped with pacing and sensing electrodes shown as a tip electrode 228 and a ring electrode 230. RV lead 206 is further shown to carry defibrillation electrodes 224 and 226, which may be elongated coil electrodes used to deliver high voltage CV/DF pulses. Defibrillation electrode 224 may be referred to herein as the "RV defibrillation electrode" or "RV coil electrode" because it may be carried along RV lead 206 such that it is positioned substantially within the right ventricle when distal pacing and sensing electrodes 228 and 230 are positioned for pacing and sensing in the right ventricle. Defibrillation electrode 226 may be referred to herein as a "superior vena cava (SVC) defibrillation electrode" or "SVC coil electrode" because it may be carried along RV lead 206 such that it is positioned at least partially along the SVC when the distal end of RV lead 206 is advanced within the right ventricle.

Each of electrodes 224, 226, 228 and 230 are connected to a respective insulated conductor extending within the body of RV lead 206. The proximal end of the insulated conductors are coupled to corresponding connectors carried by proximal lead connector 216, e.g., a DF-4 connector, for providing electrical connection to ICD 214. It is understood that although ICD 214 is illustrated in FIG. 2 as a multi-chamber device coupled to RA lead 204 and CS lead 208 in addition to RV lead 206, ICD 214 may be configured as a dual-chamber device coupled to only two transvenous leads or a single-chamber device coupled to only one transvenous lead. For example, ICD 214 may be a single-chamber device coupled to RV lead 206 and may be configured to perform the TCC techniques disclosed herein using electrodes 224, 226, 228, and 230 and/or housing 215 in addition to receiving cardiac electrical signals from heart 8 and delivering electrical stimulation therapy to heart 8.

RA lead 204 is positioned such that its distal end is in the vicinity of the right atrium and the superior vena cava. Lead 204 is equipped with pacing and sensing electrodes 220 and 222, shown as a tip electrode 220 and a ring electrode 222 spaced proximally from tip electrode 220. The electrodes 220 and 222 provide sensing and pacing in the right atrium and are each connected to a respective insulated conductor within the body of RA lead 206. Each insulated conductor is coupled at its proximal end to a connector carried by proximal lead connector 210.

CS lead 208 is advanced within the vasculature of the left side of the heart via the coronary sinus (CS) and a cardiac vein (CV). CS lead 208 is shown in FIG. 2 as having one or more electrodes 232, 234 that may be used in delivering pacing and/or sensing cardiac electrical signals in the left chambers of the heart, i.e., the left ventricle and/or the left atrium. The one or more electrodes 232, 234 of CS lead 208 are coupled to respective insulated conductors within the body of CS lead 208, which provide connection to the proximal lead connector 218.

Any of electrodes 220, 222, 224, 226, 228, 230, 232, 234 may be selected by ICD 214 in a TCC electrode vector for transmitting and/or receiving TCC signals. In some examples, housing 215 is selected in a TCC transmitting electrode vector along with a lead-based defibrillation electrode, e.g., RV coil electrode 224 or SVC coil electrode 226, to provide a low impedance and high transimpedance TCC transmitting electrode vector. In other examples, TCC transmission is performed using the RV coil electrode 224 and the SVC coil electrode 226. In still other examples, an electrode 232 or 234 carried by the CS lead 208 may be selected in combination with housing 215, RV coil electrode 224, or SVC coil electrode 226. It is recognized that numerous TCC transmitting electrode vectors may be available using the various electrodes carried by one or more of leads 204, 206 and 208 coupled to ICD 214. In some examples, multiple vectors may be selected to promote transmission via a vector that is substantially parallel to the housing-based electrodes of pacemaker 100 or to receiving electrodes of leadless pressure sensor 50 for transmitting signals to the respective pacemaker 100 or pressure sensor 50.

Housing 215 encloses internal circuitry generally corresponding to the various circuits and components described in conjunction with FIG. 5 below, for sensing cardiac signals from heart 8, detecting arrhythmias, controlling therapy delivery and performing TCC with pacemaker 100 and/or pressure sensor 50 using the techniques disclosed herein. It is recognized that these TCC transmission techniques may be practiced in conjunction with alternative lead and electrode configurations other than those depicted in the examples of FIG. 1 and FIG. 2.

Pressure sensor 50 may be implanted in the pulmonary artery of the patient for monitoring the pulmonary arterial pressure as an indication of the hemodynamic status of the patient 12. One example of pressure sensor 50 is described below in conjunction with FIG. 4. Pressure sensor 50 may be configured to receive pressure signals via a pressure sensor and receive TCC signals via a TCC receiver coupled to electrodes carried by pressure sensor 50.

In the examples of FIGS. 1 and 2, two or more IMDs may be co-implanted in a patient and communicate to enable a system level of functionality such as sharing the detection of arrhythmias between devices, synchronized timing of antitachyarrhythmia shocks, ATP, and/or post-shock pacing, optimization of the resources (e.g., battery capacity or processing power) available to each device, or sharing or coordination of physiological signal acquisition. In some examples, communication between the ICD 14 or ICD 214 and pacemaker 100 may be used to initiate therapy and/or confirm that therapy should be delivered. Communication between ICD 14 or ICD 214 and pressure sensor 50 may be used to initiate pressure signal acquisition and/or retrieval of pressure signal data from pressure sensor 50. One approach is for ICD 14 or 214 to function as a control device and pacemaker 100 and/or sensor 50 to function as responders. For instance, a TCC signal from ICD 14 or 214 may cause pacemaker 100 to deliver a cardiac pacing pulse or therapy.

In another example, ICD 214 may transmit a TCC command signal to pressure sensor 50 for causing pressure sensor 50 to begin acquiring a pressure signal. Pressure sensor 50 may be configured to transmit pressure signal data via TCC to ICD 214 or to external device 40 (shown in FIG. 1). ICD 214 may transmit a TCC command to pressure sensor 50 to cause pressure sensor 50 to transmit a pressure signal in real time, transmit a pressure signal previously acquired and stored by pressure sensor 50, or transmit pressure data derived from a pressure signal received by pressure sensor 50. In other examples, pressure sensor 50 may be configured to transmit pressure signal data via RF telemetry to ICD 214 and/or to an external device, such as device 40 shown in FIG. 1 in response to a TCC command signal received from ICD 214.

During TCC signal transmission, current is driven through the patient's body tissue between two or more electrodes of the transmitting IMD (e.g., ICD 14 or 214). The current spreads through the patient's body, e.g., through the thorax, producing a potential field. The receiving IMD (e.g., pacemaker 100 or sensor 50) may detect the TCC signal by measuring the potential difference between two of its electrodes, e.g., two housing-based electrodes of pacemaker 100 or sensor 50. Optimally, the receiving electrodes are parallel to the tissue conduction pathway of the injected current to maximize the potential difference developed on the receiving electrode vector. The current injected to transmit the TCC signal is of sufficient amplitude to produce a voltage potential that can be detected by an intended receiving IMD but should at the same time not capture excitable body tissue, e.g., causing unintended stimulation of nerve or muscle tissue, possibly leading to muscle contraction, pain and even cardiac capture.

In some cases, a co-implanted IMD may be an unintended receiver of the TCC signal. If a co-implanted IMD includes electrodes or is coupled to electrodes for receiving electrical signals, but is not the intended receiver of a TCC signal, a voltage potential may develop across the electrodes of the unintended receiver leading to interference with the normal signal detection functions of the unintended receiver. For example, in system 200, ICD 214 and pressure sensor 50 may be configured to communicate using TCC. Pacemaker 100 may be co-implanted with ICD 214 and pressure sensor 50 but not configured to send or receive TCC signals. A TCC signal transmitted by ICD 214 to pressure sensor 50 may result in voltage developed across the housing-based electrodes of pacemaker 100. Pacemaker 100 may be an unintended receiver of the transmitted TCC signal. The voltage developed across the housing-based electrodes of pacemaker 100 may interfere with a cardiac event detector included in pacemaker 100. In other examples, a subcutaneous cardiac electrical signal monitor having housing-based electrodes for monitoring a subcutaneously-acquired electrocardiogram (ECG) signal, such as the REVEAL LINQ™ Insertable Cardiac Monitor (available from Medtronic, Inc., Minneapolis, Minn., USA) may be implanted in a patient having two other IMDs configured to communicate via TCC, such as ICD 214 and pressure sensor 50. The cardiac electrical signal monitor may be an unintended receiver of TCC signals transmitted between ICD 214 and pressure sensor 50. The methods disclosed herein for transmitting TCC signals may eliminate or reduce interference of TCC signals with electrical signal sensing circuitry of other IMDs or external devices in or on the patient, which may be intended or unintended receivers.

While particular IMD systems 10 and 200, including an ICD 14 or 214, respectively, pacemaker 100 and/or pressure sensor 50 are shown in the illustrative examples of FIGS. 1 and 2, methodologies described herein for TCC transmission may be used with other IMD systems including other types and locations of IMDs as well as other lead and electrode arrangements. For example, an implantable cardiac monitor, such as the REVEAL LINQ™ Insertable Cardiac Monitor, may be utilized as a relay device for leadless pacemaker 100 and/or pressure sensor 50 by receiving data from those devices via TCC and transmitting that data to an external device 40 via RF communication, such as BLUETOOTH™ communication. Generally, this disclosure describes various techniques for transmitting TCC signals by an IMD and for receiving TCC signals by a co-implanted IMD (or external device). The TCC signal transmission and receiving techniques promote reliable communication via TCC signals between two medical devices for transferring multiple bytes of data during a transmission session while avoiding unintended tissue stimulation. The TCC techniques may also reduce the likelihood of TCC signal oversensing by sensing circuitry included in the transmitting device and/or another IMD co-implanted with the transmitting device. Another IMD co-implanted with the transmitting device may be the intended receiving device of the TCC signal transmission or another IMD that is not the targeted recipient and may not even be configured to receive and detect TCC communication signals.

Figure 3A:
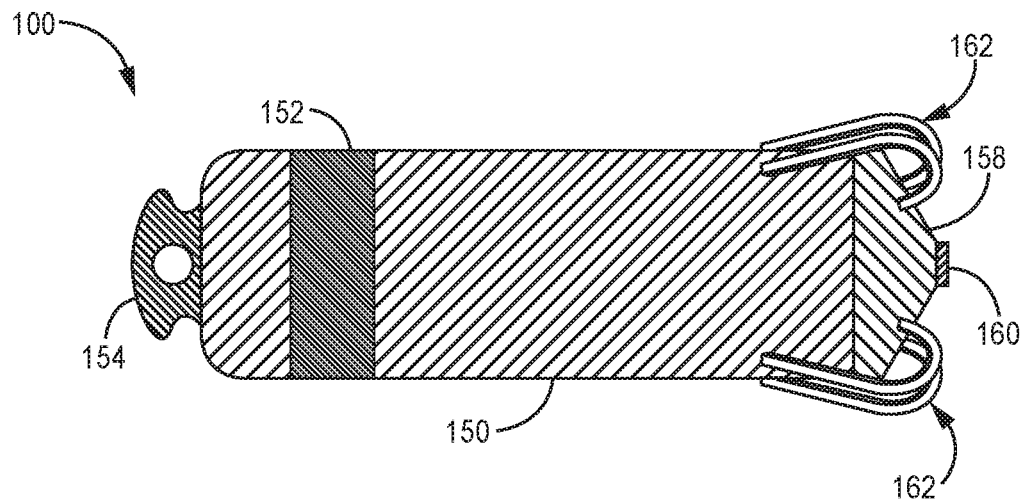
FIG. 3A is a conceptual diagram of a leadless intracardiac pacemaker according to one example.

FIG. 3A is a conceptual diagram of pacemaker 100 according to one example. As shown in FIG. 3A, pacemaker 100 may be a leadless pacemaker including a housing 150, housing end cap 158, distal electrode 160, proximal electrode 152, fixation member 162, and a delivery tool interface member 154. Housing 150, sealed with end cap 158, encloses and protects the various electrical components within pacemaker 100. Pacemaker 100 is shown including two electrodes 152 and 160 but may include two or more electrodes for delivering cardiac electrical stimulation pulses (such as pacing pulses or ATP), sensing cardiac electrical signals for detecting cardiac electrical events, and for receiving and/or transmitting TCC signals.

Electrodes 152 and 160 are carried on the housing 150 and housing end cap 158. In this manner, electrodes 152 and 160 may be considered housing-based electrodes. In other examples, one or more electrodes may be coupled to circuitry enclosed by housing 150 via an electrode extension extending away from housing 150. In the example of FIG. 3A, electrode 160 is disposed on the exterior surface of end cap 158. Electrode 160 may be a tip electrode positioned to contact cardiac tissue upon implantation and fixation at a pacing site by fixation member 162. Electrode 152 may be a ring or cylindrical electrode disposed along the exterior surface of housing 150. Both housing 150 and housing end cap 158 may be electrically insulating. In some examples, housing 150 is an electrically conductive material, e.g., a titanium alloy or other biocompatible metal or metal alloy. Portions of housing 150 may be coated with a non-conductive material, e.g., parylene, polyurethane, silicone or other biocompatible polymer, to insulate portions of housing 150 not functioning as electrode 152.

Electrodes 160 and 152 may be used as a cathode and anode pair for cardiac pacing therapy and receiving and/or transmitting TCC signals. In addition, electrodes 152 and 160 may be used to detect intrinsic electrical signals from the patient's heart 8. In other examples, pacemaker 100 may include three or more electrodes, where any two or more of the electrodes may be selected to form a vector for delivery of electrical stimulation therapy, detecting intrinsic cardiac electrical signals from the patient's heart 8, transmitting TCC signals, and receiving TCC signals. In some examples in which pacemaker 100 includes three or more electrodes, two or more of the electrodes may be selected, e.g., via switches, to form a vector for TCC. Pacemaker 100 may use multiple vectors for TCC transmission or receiving, for example, to promote a substantially parallel electrical configuration with a TCC transmitting electrode vector of ICD 14 or ICD 214, which may increase the transimpedance and increase the received voltage signal.

Fixation member 162 may include multiple tines of a shape memory material that retains a preformed curved shape as shown. During implantation, fixation member 162 may be flexed forward to pierce tissue and elastically flex back towards housing 150 to regain their pre-formed curved shape. In this manner, fixation member 162 may be embedded within cardiac tissue at the implant site. In other examples, fixation member 162 may include helical fixation tines, barbs, hooks or other fixation features.

Delivery tool interface member 154 may be provided for engaging with a delivery tool used to advance pacemaker 100 to an implant site. A delivery tool may be removably coupled to delivery tool interface member 154 for retrieving pacemaker 100 back into a delivery tool if removal or repositioning of pacemaker 100 is required.

Figure 3B:
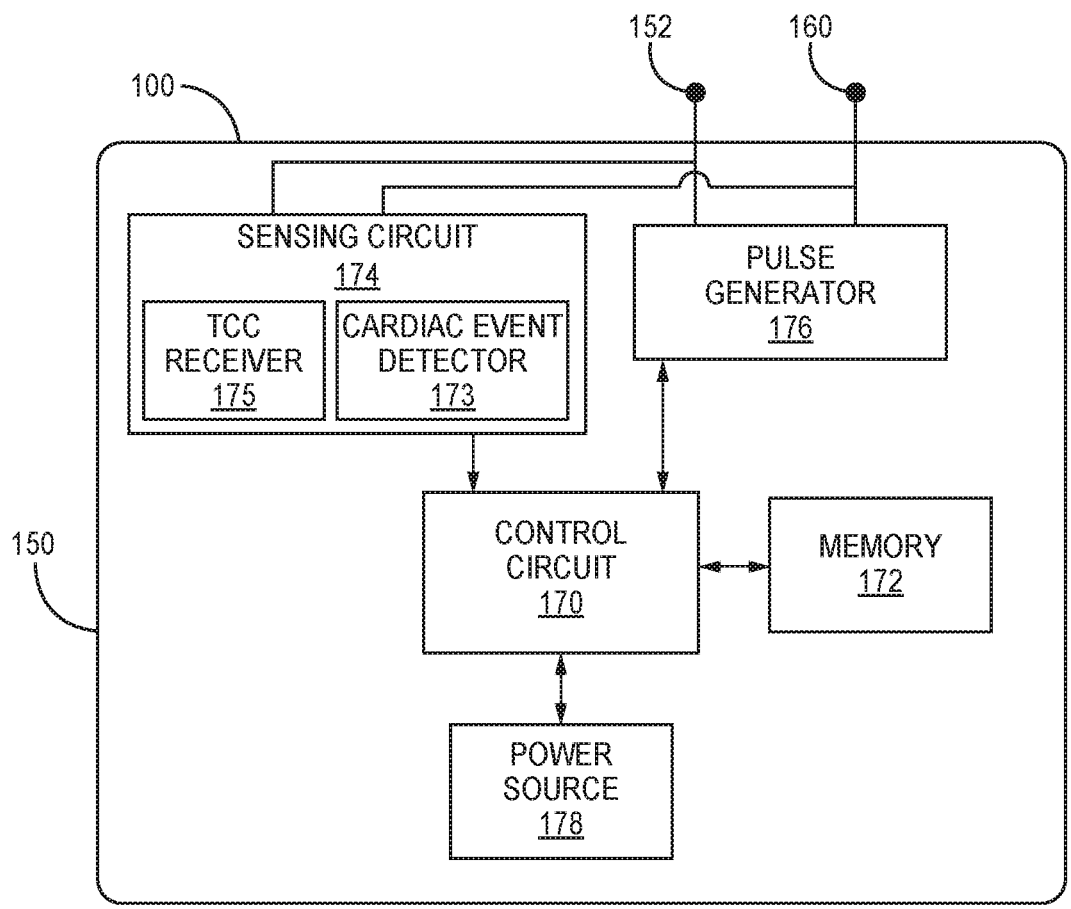
FIG. 3B is a schematic diagram of circuitry that may be included in the pacemaker of FIG. 3A according to one example.

FIG. 3B is a schematic diagram of circuitry that may be enclosed by pacemaker housing 150 according to one example. Pacemaker housing 150 may enclose a control circuit 170, memory 172, pulse generator 176, sensing circuit 174, and a power source 178. Control circuit 170 may include a microprocessor and/or other control circuitry for controlling the functions attributed to pacemaker 100 herein, such as controlling pulse generator 176 to deliver signals via electrodes 152 and 160 and controlling sensing circuit 174 to detect signals from electrical signals received via electrodes 152 and 160. Power source 178 may include one or more rechargeable or non-rechargeable batteries for providing power to control circuit 170, memory 172, pulse generator 176 and sensing circuit 174 as needed. Control circuit 170 may execute instructions stored in memory 172 and may control pulse generator 176 and sensing circuit 174 according to control parameters stored in memory 172, such as various timing intervals, pacing pulse parameters and cardiac event sensing parameters.

Pulse generator 176 generates therapeutic pacing pulses delivered via electrodes 152 and 160 under the control of timing circuitry included in control circuit 170. Pulse generator 176 may include charging circuitry, one or more charge storage devices such as one or more capacitors, and switching circuitry that couples the charge storage device(s) to an output capacitor coupled to electrodes 160 and 152 to discharge the charge storage devices via electrodes 160 and 152. In some examples, pulse generator includes a TCC transmitter (standalone or as part of a transceiver), such as the transmitter described below in conjunction with FIG. 6, for generating TCC signals transmitted via electrodes 160 and 152. Power source 178 provides power to the charging circuit of pulse generator 176 and the TCC transmitter when present.

Pacemaker 100 may be configured for sensing cardiac electrical signals, e.g., R-waves or P-waves, and include a cardiac event detector 173. Intrinsic cardiac electrical events may be detected from an electrical signal produced by the heart and received via electrodes 152 and 160. Cardiac event detector 173 may include filters, amplifiers, an analog-to-digital converter, rectifier, comparator, sense amplifier or other circuitry for detecting cardiac events from a cardiac electrical signal received via electrodes 152 and 160. Under the control of control circuit 170, cardiac event detector 173 may apply various blanking and/or refractory periods to circuitry included in event detector 173 and an auto-adjusting cardiac event detection threshold amplitude, e.g., an R-wave detection threshold amplitude or a P-wave detection threshold amplitude, to the electrical signal received via electrodes 152 and 160.

Sensing circuit 174 may further include a TCC signal detector 175 for detecting a TCC signal from ICD 14 (or ICD 214). A voltage potential develops across electrodes 152 and 160 in response to current conducted via a tissue pathway during TCC signal transmission from ICD 14 or ICD 214. The voltage signal may be received and demodulated by TCC signal detector 175 and decoded by control circuit 170. TCC signal detector 175 may include amplifiers, filters, analog-to-digital converters, rectifiers, comparators, counters, a phase locked loop and/or other circuitry configured to detect a wakeup beacon signal from a transmitting device and detect and demodulate the modulated carrier signal transmitted in data packets including encoded data. For example, TCC signal detector 175 of pacemaker 100 (and other TCC signal detectors referred to herein) may include a pre-amplifier and a high-Q filter tuned to the carrier frequency of a carrier signal that is used to transmit beacon signals and data signals during a TCC transmission session. The filter may be followed by another amplifier and a demodulator that converts the received signal to a binary signal representing coded data.

The circuitry of TCC signal detector 175 may include circuitry shared with cardiac event detector 173 in some examples. The filters included in TCC signal detector 175 and cardiac event detector 173, however, are expected to operate at different passbands, for example, for detecting different signal frequencies. The TCC signals may be transmitted with a carrier frequency in the range of 33 to 250 kHz, in the range of 60 to 200 kHz, or at 100 kHz as examples. Cardiac electrical signals generated by heart 8 are generally less than 100 Hz. The TCC signal transmission techniques disclosed herein may reduce or eliminate oversensing of a received TCC signal, e.g., transmitted from ICD 14 or ICD 214, as a cardiac electrical event by cardiac event detector 173. In examples that include a TCC transmitter in pacemaker 100, the TCC signal transmission techniques disclosed herein may reduce or prevent oversensing of a TCC signal produced by the TCC transmitter and transmitted via electrodes 152 and 160 from being detected as a cardiac event by cardiac event detector 173. In some instances, the TCC transmitter may include circuitry shared with pulse generator 176, such that the TCC signals are transmitted using the pacing circuitry of pacemaker 100 and/or transmitted as sub-threshold pacing pulses or pacing pulses that occur during the refractory period of the heart.

In other examples, pacemaker 100 may include fewer or more components than the circuits and components shown in FIG. 3B. For instance, pacemaker 100 may include other physiological sensors and/or an RF telemetry circuit for communication with external device 40 instead of or in addition to TCC signal detector 175 and a TCC transmitter (if included).

Figure 4:
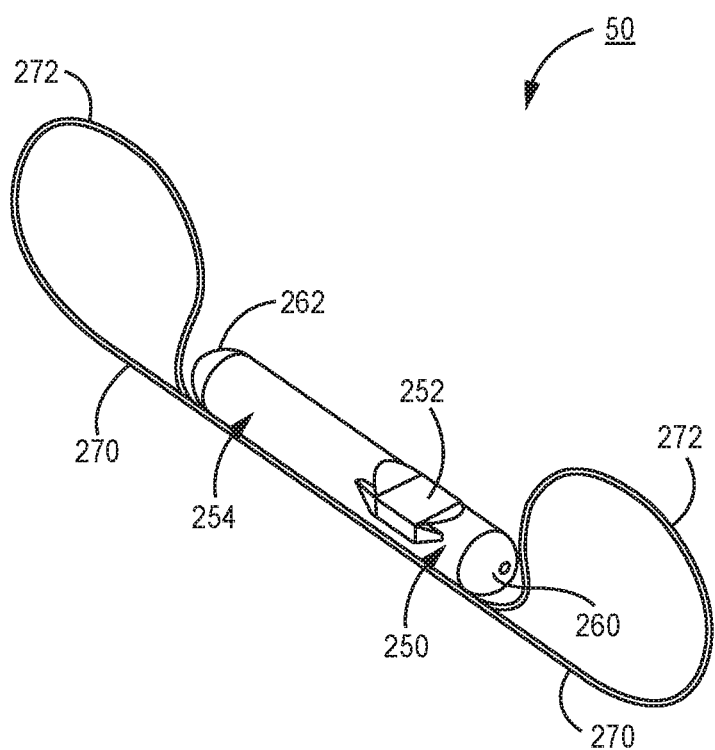
FIG. 4 illustrates a perspective view of a leadless pressure sensor according to one example.

FIG. 4 illustrates a perspective view of leadless pressure sensor 50 according to one example. Leadless pressure sensor 50 may generally correspond to the IMD disclosed in U.S. Pat. Publication No. 2012/0323099 A1 (Mothilal, et al.), incorporated herein by reference in its entirety. As shown in FIG. 4, pressure sensor 50 includes an elongated housing 250 having a pressure sensitive diaphragm or window 252 that exposes a pressure sensitive element within housing 250 to the surrounding pressure. Electrodes 260 and 262 may be secured to opposite ends of housing 250 and may be electrically insulated from housing 250 to form an electrode pair for receiving TCC signals. Electrodes 260 and 262 may be coupled to a TCC signal detector (corresponding to the TCC signal detector 175 described above) enclosed by housing 250 for detecting and demodulating TCC signals received from ICD 14 or 214.

Housing 250 may enclose a battery, a pressure sensing circuit, a TCC signal detector, control circuitry, and memory for storing pressure signal data. In some examples, the pressure sensing circuit includes an air gap capacitive element and associated circuitry, which may include temperature compensation circuitry, for producing a signal correlated to pressure along window 252. The pressure sensing circuit and window 252 may correspond to a pressure sensor module as generally disclosed in U.S. Pat. No. 8,720,276 (Kuhn, et al.), incorporated herein by reference in its entirety. The pressure sensing circuit may include a micro electro-mechanical system (MEMS) device in some examples. A fixation member 270 extends from housing 250 and may include a self-expanding stent or one or more self-expanding loops 272 that stabilize the position of pressure sensor 50 along an artery, such as the pulmonary artery, by gently pressing against the interior walls of the artery.

When deployed in an arterial location, pressure sensor 50 produces and stores pressure signals correlated to arterial blood pressure.

Figure 6:
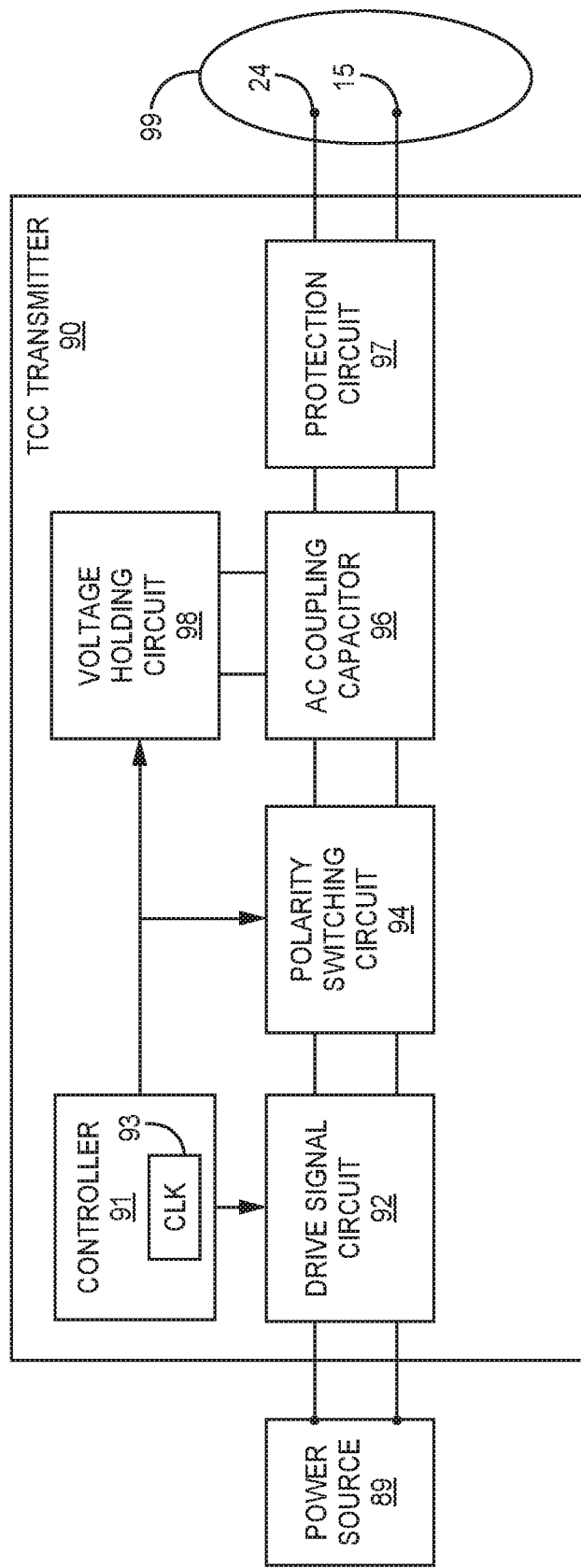
FIG. 6 is a conceptual diagram illustrating an example configuration of a TCC transmitter that may be included in the ICD of FIG. 5 or in the pacemaker of FIG. 3B or pressure sensor of FIG. 4.

In some examples, pressure sensor 50 includes a TCC transmitter, such as the transmitter shown in FIG. 6, for transmitting TCC signals to another medical device, such as ICD 14 or ICD 214, pacemaker 100 or external device 40. Pressure sensor 50 may transmit a pressure signal, data extracted from a pressure signal or other communication data in a TCC signal via electrodes 260 and 262. For instance, pressure sensor 50 may include a TCC transmitter for at least producing acknowledgment and/or confirmation signals transmitted back to a transmitting device, e.g., ICD 14 or ICD 214, in response to receiving a TCC signal to confirm detection of a beacon signal and/or reception of transmitted data packets.

Figure 5:
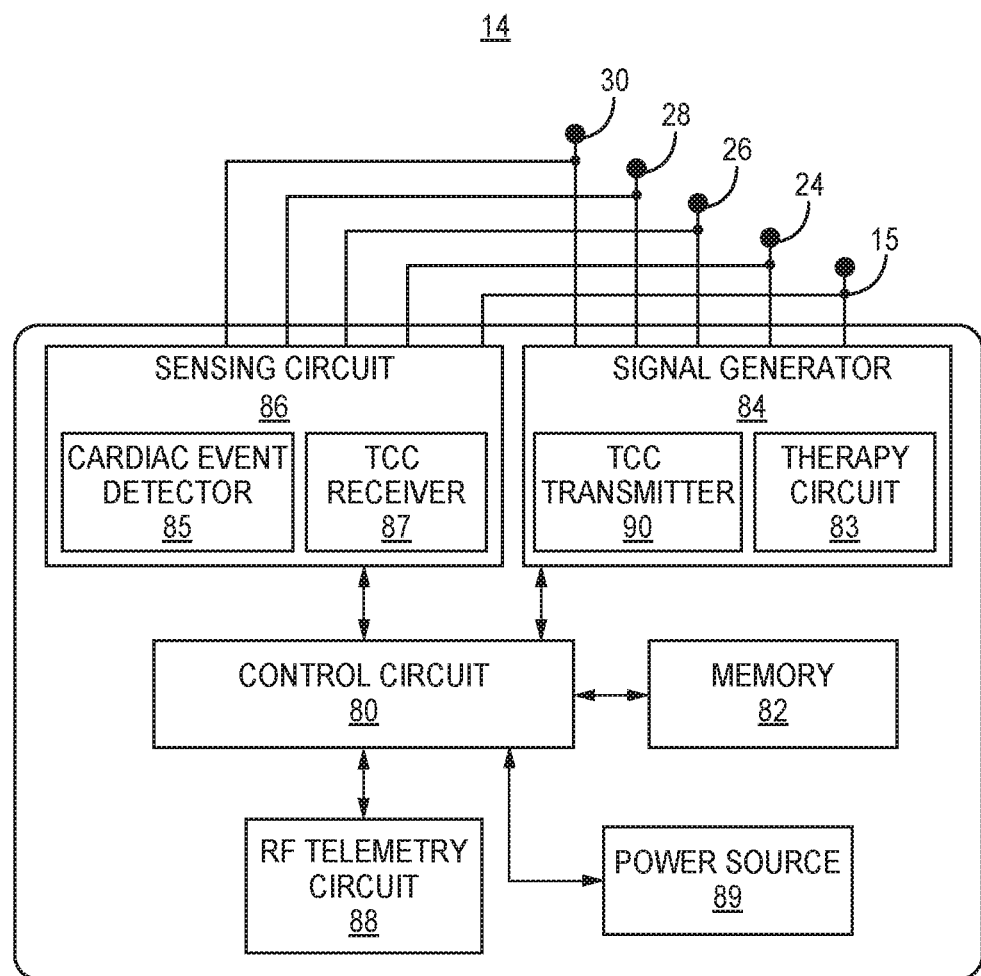
FIG. 5 is a schematic diagram of an ICD capable of transmitting TCC signals according to one example.

FIG. 5 is a schematic diagram of an ICD capable of transmitting TCC signals according to one example. For illustrative purposes, ICD 14 of FIG. 1 is depicted in FIG. 5 coupled to electrodes 24, 26, 28, and 30, with housing 15 represented schematically as an electrode. It is to be understood, however, that the circuitry shown in FIG. 5 may generally correspond to circuitry included in ICD 214 of FIG. 2 and adapted accordingly for single, dual, or multi-chamber cardiac signal sensing and therapy delivery functions using electrodes carried by transvenous leads. For instance, in the example of the multi-chamber ICD 214 of FIG. 2, signal generator 84 may include multiple therapy delivery output channels and sensing circuit 86 may include multiple sensing channels each selectively coupled to respective electrodes of RA lead 204, RV lead 206 and CS lead 208, corresponding to each cardiac chamber, e.g., the right atrium, the right ventricle, and the left ventricle.

The ICD circuitry may include a control circuit 80, memory 82, signal generator 84, sensing circuit 86, and RF telemetry circuit 88. A power source 89 provides power to the circuitry of the ICD, including each of the circuits 80, 82, 84, 86, and 88 as needed. Power source 89 may include one or more energy storage devices, such as one or more rechargeable or non-rechargeable batteries. The connections between power source 89 and each of the other circuits 80, 82, 84, 86 and 88 are to be understood from the general block diagram of FIG. 5, but are not shown for the sake of clarity. For example, power source 89 may be coupled to charging circuits included in signal generator 84 for charging capacitors or other charge storage devices included in therapy circuit 85 for producing electrical stimulation pulses such as CV/DF shock pulses or pacing pulses. Power source 89 is coupled to TCC transmitter 90 for providing power for generating TCC signals. Power source 89 provides power to processors and other components of control circuit 80, memory 82, amplifiers, analog-to-digital converters and other components of sensing circuit 86, and a transceiver of RF telemetry circuit 88, as examples.

Memory 82 may store computer-readable instructions that, when executed by a processor included in control circuit 80, cause ICD 14 to perform various functions attributed to ICD 14 (e.g., detection of arrhythmias, communication with pacemaker 100 or pressure sensor 50, and/or delivery of electrical stimulation therapy). Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Control circuit 80 communicates with signal generator 84 and sensing circuit 86 for sensing cardiac electrical activity, detecting cardiac rhythms, and controlling delivery of cardiac electrical stimulation therapies in response to sensed cardiac signals. The functional blocks shown in FIG. 5 represent functionality included in ICD 14 (or ICD 214) and may include any discrete and/or integrated electronic circuit components that implement analog and/or digital circuits capable of producing the functions attributed to ICD 14 herein. Providing software, hardware, and/or firmware to accomplish the described functionality in the context of any modern IMD system, given the disclosure herein, is within the abilities of one of skill in the art.

Sensing circuit 86 may be selectively coupled to electrodes 24, 26, 28, 30 and/or housing 15 in order to monitor electrical activity of the patient's heart 8. Sensing module 86 may include switching circuitry for selecting which of electrodes 24, 26, 28, 30 and housing 15 are coupled to sense amplifiers or other cardiac event detection circuitry included in cardiac event detector 85. Switching circuitry may include a switch array, switch matrix, multiplexer, or any other type of switching device suitable to selectively couple sense amplifiers to selected electrodes. The cardiac event detector 85 within sensing circuit 86 may include one or more sense amplifiers, filters, rectifiers, threshold detectors, comparators, analog-to-digital converters (ADCs), or other analog or digital components configured to detect cardiac electrical events from a cardiac electrical signal received from heart 8.

In some examples, sensing circuit 86 includes multiple sensing channels for acquiring cardiac electrical signals from multiple sensing vectors selected from electrodes 24, 25, 28, 30 and housing 15. Each sensing channel may be configured to amplify, filter, digitize and rectify the cardiac electrical signal received from selected electrodes coupled to the respective sensing channel to improve the signal quality for sensing cardiac events, e.g., P-waves attendant to atrial depolarizations and/or R-waves attendant to ventricular depolarizations. For example, each sensing channel in sensing circuit 86 may include an input or pre-filter and amplifier for receiving a cardiac electrical signal developed across a selected sensing electrode vector, an analog-to-digital converter, a post-amplifier and filter, and a rectifier to produce a filtered, digitized, rectified and amplified cardiac electrical signal that is passed to a cardiac event detector included in sensing circuit 86. The cardiac event detector 85 may include a sense amplifier, comparator or other circuitry for comparing the rectified cardiac electrical signal to a cardiac event sensing threshold, such as an R-wave sensing threshold amplitude, which may be an auto-adjusting threshold. Sensing circuit 86 may produce a sensed cardiac event signal in response to a sensing threshold crossing. The sensed cardiac events, e.g., R-waves and/or P-waves, are used for detecting cardiac rhythms and determining a need for therapy by control circuit 80. ICD 214 of FIG. 2 may include a sensing circuit having a separate atrial sensing channel for sensing P-waves using atrial electrodes and a ventricular sensing channel for sensing R-waves using ventricular electrodes.

Control circuit 80 may include interval counters, which may be reset upon receipt of a cardiac sensed event signal from sensing circuit 86. The value of the count present in an interval counter when reset by a sensed R-wave or P-wave may be used by control circuit 80 to measure the durations of R-R intervals, P-P intervals, P-R intervals and R-P intervals, which are measurements that may be stored in memory 82. Control circuit 80 may use the count in the interval counters to detect a tachyarrhythmia event, such as atrial fibrillation (AF), atrial tachycardia (AT), VF or VT.

These intervals may also be used to detect the overall heart rate, ventricular contraction rate, and heart rate variability.

Signal generator 84 includes a therapy circuit 92 and a TCC transmitter 90. The therapy circuit 92 is configured to generate cardiac electrical stimulation pulses, e.g., CV/DF shock pulses and cardiac pacing pulses for delivery to heart 8 via electrodes carried by lead 16 (and in some cases housing 15). Signal generator 84 may include one or more energy storage elements, such as one or more capacitors, configured to store the energy required for a therapeutic CV/DF shock or pacing pulse. In response to detecting a shockable tachyarrhythmia, control circuit 80 controls therapy circuit 83 to charge the energy storage element(s) to prepare for delivering a CV/DF shock. Therapy circuit 83 may include other circuitry, such as charging circuitry, which may include a transformer and/or a charge pump, to charge the energy storage element, and switches to couple the energy storage element to an output capacitor to discharge and deliver the CV/DF shock and change the polarity of the shock to provide a bi-phasic or multi-phasic shock. Therapy circuit 83 may include a variety of voltage level-shifting circuitry, switches, transistors, diodes, or other circuitry. Therapy circuit 83 may include switching circuitry for selecting a shock delivery vector and delivers the shock therapy to the patient's heart 8 via the shock delivery vector, e.g., two or more electrodes such as defibrillation electrode 24 or 26 and housing 15.

In some examples, therapy circuit 83 may include both a low voltage therapy circuit for generating and delivering relatively low voltage therapy pulses, such as pacing pulses, and a high voltage therapy circuit for generating and delivering CV/DF shocks. Low voltage pacing pulses may be delivered via a pacing electrode vector selected from electrodes 24, 26, 28, 30 and housing 15. Pacing pulses may be delivered when a pacing escape interval set by a pace timing circuit of control circuit 80 times out without a sensed cardiac event causing the escape interval to be reset. The pace timing circuit may set various escape intervals for timing pacing pulses, e.g., to provide bradycardia pacing or post-shock pacing, or in response to detecting a tachyarrhythmia by delivering ATP. In some examples, pacemaker 100 is provided for delivering at least some low voltage pacing therapies, e.g., when signaled to do so by a TCC signal transmitted from ICD 14. A low voltage therapy circuit included in ICD 214 of FIG. 2 may include multiple pacing channels, including an atrial pacing channel, a right ventricular pacing channel, and a left ventricular pacing channel, to provide single, dual or multi-chamber pacing in addition to the high voltage therapy circuit used for delivering CV/DF shocks.

In some examples, ICD 14 (or ICD 214) is configured to monitor the impedance of an electrode vector. For example, signal generator 84 may apply a current drive signal to a pair of electrodes coupled to ICD 14. Sensing circuit 86 may detect the resulting voltage developed across the pair of electrodes. Impedance monitoring may be performed for detecting a lead or electrode issue and for selecting a therapy delivery electrode vector, a TCC transmitting electrode vector, or a sensing electrode vector based at least in part on the lead/electrode impedance. In other examples, ICD 14 or ICD 214 may be configured to monitor bioimpedance in a tissue volume, e.g., thoracic impedance or cardiac impedance, for monitoring a patient condition.

TCC transmitter 90 is configured to generate TCC signals for transmission from a transmitting electrode vector selected from the electrodes 24, 26, 28, 30 and housing 15 via a conductive tissue pathway. TCC transmitter 90 is configured to generate and transmit a TCC signal, e.g., to communicate with pacemaker 100, sensor 50 or another IMD, or an external device 40. In some examples, signal generator 84 includes switching circuitry for selectively coupling TCC transmitter 90 to a selected transmitting electrode vector, e.g., using any two or more of electrodes 24, 26, 28, 30 and housing 15, e.g., housing 15 and defibrillation electrode 24, for transmission of a TCC signal.

The TCC signal may be transmitted having a carrier signal with a peak-to-peak amplitude and carrier frequency selected to avoid stimulation of excitable tissue of patient 12. In some examples, the carrier frequency of the TCC signal may be 100 kilohertz (kHz) or higher. A TCC signal emitted or received, for example by electrode 24 and housing 15, at a frequency of at least approximately 100 kHz may be less likely to stimulate nearby tissue, e.g., muscles or nerves, or cause pain than lower frequency waveforms. Consequently, a TCC signal having a frequency of at least approximately 100 kHz may have a higher amplitude than a lower frequency signal without causing extraneous nerve or muscle stimulation. A relatively higher amplitude signal may increase the likelihood that pacemaker 100, pressure sensor 50 or another implanted or external device, may receive the TCC signal from ICD 14 (or ICD 214). The peak-to-peak amplitude of the TCC signal may be within a range from approximately 100 microamps to 10 milliamps (mA) or more, such as within a range from approximately 1 mA to approximately 10 mA. In some examples, the amplitude of the TCC signal may be approximately 3 mA. A TCC signal having a frequency of at least approximately 100 kHz and an amplitude no greater than approximately 10 mA may be unlikely to stimulate nearby tissue, e.g., muscles or nerves, or cause pain. For a transmitting electrode vector having an impedance of 200 ohms injecting a current signal having an amplitude of 10 mA peak-to-peak, the voltage signal at the transmitting electrode vector may be 2 Volts peak-to-peak. The voltage developed at the receiving electrode vector may be in the range of 0.1 to 100 millivolts peak-to-peak.

The modulation of the TCC signal may be, as examples, amplitude modulation (AM), frequency modulation (FM), or digital modulation (DM), such as frequency-shift keying (FSK) or phase-shift keying (PSK). In some examples, the modulation is FM toggling between approximately 150 kHz and approximately 200 kHz. In some examples, the TCC signal has a frequency of 150/200 kHz and is modulated using FSK modulation at 12.5 kbps. In the illustrative examples presented herein a TCC signal having a carrier frequency of 100 kHz is modulated to encode data using binary phase shift keying (BPSK). Balanced pulses of opposite polarity may be used to shift the phase of the TCC signal, e.g., by 180 degrees positively or negatively, and balance the charge injected into the body tissue during the phase shift to reduce the likelihood of interfering with cardiac event sensing operations of the cardiac event detector 85. Techniques for BPSK modulation of the TCC carrier signal using charge balanced phase shifts are disclosed in U.S. patent application Ser. No. 16/202,418 (Roberts, et al.) incorporated herein by reference in its entirety. The data modulated on TCC signals, e.g., being sent to pacemaker 100 or pressure sensor 50, may include "wakeup" commands, commands to deliver a therapy, and/or commands to collect or send physiological signal data, as examples.

The configuration of signal generator 84 including TCC transmitter 90 illustrated in FIG. 5 may provide "one-way" or uni-directional TCC. Such a configuration may be used if, for example, the ICD 14 is configured as a control device to transmit a command or request to another IMD configured as a responder, e.g., to pacemaker 100 or sensor 50 to provide commands for pacing delivery or pressure signal acquisition, for instance. In some examples, sensing circuit 86 may include a TCC receiver 87 to facilitate "two-way" TCC between the ICD and another IMD. ICD 14 or ICD 214 may be configured to receive confirmation signals from the intended receiving device to confirm that a transmitted TCC signal was successfully received. In other examples, ICD 14 or ICD 214 may receive commands via TCC receiver 87 from another IMD or external device. The TCC receiver 87 may have more sensitivity than an RF telemetry circuit 88, e.g., to compensate for lower signal-to-noise ratio signals from a transmitting device such as pacemaker 100 or sensor 50. For instance, pacemaker 100 may generate relatively low signal-to-noise ratio signals by generating relatively small amplitude signals due to its smaller power source, and/or to avoid stimulation of adjacent cardiac tissue. A modulated or unmodulated carrier signal may be received by TCC receiver 87 via electrodes selectively coupled to sensing circuit 86. TCC receiver 87 may include an amplifier, filter and demodulator to pass the demodulated signal, e.g., as a stream of digital values, to control circuit 80 for decoding of the received signal and further processing as needed.

In other examples, TCC receiver 87 and/or TCC transmitter 90 may be distinct components separate from sensing circuit 86 and signal generator 84, respectively. For example, ICD 14 may include a TCC transceiver that incorporates the circuitry of TCC receiver 87 and/or TCC transmitter 90. In this case, the functionality described with respect to TCC receiver 87 and/or TCC transmitter 90 may be performed via a distinct TCC component instead of being part of sensing circuit 86 and signal generator 84.

Memory 82 may be configured to store a variety of operational parameters, therapy parameters, sensed and detected data, and any other information related to the monitoring, therapy and treatment of patient 12. Memory 82 may store, for example, thresholds and parameters indicative of tachyarrhythmias and/or therapy parameter values that at least partially define delivered anti-tachyarrhythmia shocks and pacing pulses. In some examples, memory 82 may also store communications transmitted to and/or received from pacemaker 100, pressure sensor 50 or another device.

ICD 14 may have an RF telemetry circuit 88 including an antenna and transceiver for RF telemetry communication with external device 40. RF telemetry circuit 88 may include an oscillator and/or other circuitry configured to generate a carrier signal at the desired frequency. RF telemetry circuit 88 further includes circuitry configured to modulate data, e.g., stored physiological and/or therapy delivery data, on the carrier signal. The modulation of RF telemetry signals may be, as examples, AM, FM, or DM, such as FSK or PSK.

In some examples, RF telemetry circuit 88 is configured to modulate the TCC signal for transmission by TCC transmitter 90. Although RF telemetry circuit 88 may be configured to modulate and/or demodulate both RF telemetry signals and TCC signals within the same frequency band, e.g., within a range from approximately 150 kHz to approximately 200 kHz, the modulation techniques for the two signals may be different. In other examples, TCC transmitter 90 includes a modulator for modulating the TCC signal and/or TCC receiver 87 includes a demodulator for modulating the TCC signal rather than RF telemetry circuit 88.

FIG. 6 is a conceptual diagram of TCC transmitter 90 according to one example. TCC transmitter 90 (or transmitter portion of a transceiver) may include a controller 91, drive signal circuit 92, polarity switching circuit 94, alternating current (AC) coupling capacitor 96, protection circuit 97 and voltage holding circuit 98. In other examples, TCC transmitter 90 may include fewer or more components than the circuits and components shown in FIG. 6. ICD power source 89 is shown coupled to TCC transmitter 90 to provide power necessary to generate TCC signals. While the controller 91, drive signal circuit 92, polarity switching circuit 94, AC coupling capacitor 96, protection circuit 97 and voltage holding circuit 98 are shown as discrete circuits by the blocks in FIG. 6, it is recognized that these circuits may include common components or a common circuit may perform the functions attributed to the separate circuit blocks shown in FIG. 6. For example, generating a carrier current signal having a carrier frequency and a peak-to-peak amplitude may be performed by drive signal circuit 92 and/or polarity switching circuit 94 under the control of controller 91.

In other examples, controller 91 may be implemented within control circuit 80. The clock circuit 93 may be configured to provide a clock signal that may be used to transmit the TCC signal during a transmission session using more than one frequency. For example, TCC transmitter 90 may be configured to provide a clock signal that may be used to transmit the TCC signal using at least three different frequencies, the TCC signal being modulated using FSK during a wakeup mode (e.g., modulating the signal using two different frequencies) and switch to a data transmission mode that includes transmitting data packets using a carrier signal at a third frequency (e.g., modulated using BPSK or other modulation technique) For example, during the wakeup mode a beacon signal may be transmitted using high and low alternating frequencies, which may be centered on the frequency of the carrier signal. The beacon signal may indicate the proximity or location of IMD 14 and/or its readiness to communicate. The beacon signal may be followed by a request to establish a communication, sometimes referred to as an "OPEN" request or command, transmitted at the carrier frequency. A clock signal generated by clock circuit 93 may be required to enable generation of at least three different frequencies of the TCC signal produced by drive signal circuit 92 and/or polarity switching circuit 94 and passed to AC coupling capacitor 96 in this particular example.

After switching from the wakeup mode to the transmission mode, the TCC transmitter 90 may be configured to transmit the carrier signal at the carrier frequency, different than the distinct high and low frequencies used during the beacon signal transmission. The carrier signal is modulated using BPSK in one example such that the TCC signal is transmitted using a single frequency during the data transmission mode.

The clock circuit 93 may operate at one clock frequency during the wakeup mode and at another clock frequency during the data transmission mode. For example, clock circuit 93 may be controlled to operate at the lowest possible clock frequency that can be used to generate the high frequency and low frequency cycles of the beacon signal during the wakeup mode to conserve power provided by power source 89. The clock circuit 91 may be configured to operate at a higher frequency for controlling drive signal circuit and polarity switching circuit to generate the carrier signal during signal transmission. The clock circuit frequency may be changed between the wakeup and transmission modes under the control of controller 91 using digital trim codes stored in hardware registers.

TCC transmitter 90 is shown coupled to a transmitting electrode vector 99 including defibrillation electrode 24 and housing 15 (of FIG. 1) in this example. It is to be understood that TCC transmitter 90 may be coupled to one or more TCC transmitting electrode vectors selected from any of the available electrodes coupled to the transmitting device as described above via switching circuitry included in signal generator 84. Controller 91 may be configured to switchably connect a transmitting electrode vector 99 to TCC transmitter 90 for transmission of TCC signals, e.g., by controlling switches included in signal generator 84, which may be included in TCC transmitter 90 between AC coupling capacitor 96 and transmitting electrode vector 99, e.g., in protection circuit 97. Controller 91 may select a transmitting electrode vector from among multiple electrodes coupled to the transmitting device, which may include electrodes carried by the housing of the transmitting device, a transvenous lead, e.g., any of leads 204, 206 or 208 shown in FIG. 2, or a non-transvenous lead, e.g., extra-cardiovascular lead 16 shown in FIG. 1.

Drive signal circuit 92 may include a voltage source and/or a current source powered by power source 89. In one example, drive signal circuit 92 may be an active drive signal circuit generating a balanced, bi-directional drive current signal to balance the return current with the drive current for a net zero DC current injected into the body tissue via transmitting electrode vector 99. In another example, the drive signal circuit 92 may include a charge pump and a holding capacitor that is charged by the charge pump to generate a current signal that is coupled to the transmitting electrode vector 99. In yet another example, drive signal circuit 92 may include a current source that is used to charge a holding capacitor included in drive signal circuit 92.

The drive signal generated by drive signal circuit 92 may be a voltage signal in some examples. In the illustrative examples presented herein, the drive signal circuit 92 generates a current signal to deliver TCC signal current through the transmitting electrode vector 99 having a desired peak-to-peak amplitude, e.g., high enough to produce a voltage signal on receiving electrodes of a receiving device that is detectable by the receiving device, which may be pacemaker 100, sensor 50 or another intended receiving medical device, implanted or external. The peak-to-peak current amplitude is low enough to avoid or reduce the likelihood of stimulation of tissue. A carrier signal that may be generated by drive signal circuit 92 and/or polarity switching circuit 94 may have a peak-to-peak amplitude in a range from approximately 1 mA to approximately 10 mA, such as approximately 3 mA peak-to-peak, as discussed above. The voltage developed at the receiving electrode vector may be in the range of 0.1 to 100 millivolts peak-to-peak.

Polarity switching circuit 94 receives the drive signal from drive signal circuit 92 and includes circuitry configured to switch the polarity of the drive signal current at a carrier frequency of the TCC signal. For example, polarity switching circuit 94 may include transistors and/or switches configured to switch the polarity of the drive current signal at the frequency of the TCC signal. In some examples, polarity switching circuit includes a respective one or more transistors and/or switches coupled to each of electrode 24 and housing 15, and the on-off states of the respective transistor(s) and/or switch(es) are alternated to switch the polarity of the TCC signal current between the electrodes at the carrier frequency. As discussed above, the carrier frequency may be approximately 100 kHz. For example, the carrier frequency may be within a range from approximately 33 kHz to approximately 250 kHz.

In some examples, RF telemetry module 86 may include a mixed signal integrated circuit or other circuitry configured to provide a digital version of the modulated TCC signal to controller 91. In other examples, controller 91 is configured to produce the digital input signal for modulating the TCC carrier signal to encode communication data in the transmitted signal. Controller 91 controls one or both of drive signal circuit 92 and/or polarity switching circuit 94 to modulate the TCC carrier frequency signal to generate the modulated TCC signal with an amplitude, phase shifts, and/or frequency according to the encoding. For example, controller 91 may control polarity switching circuit 94 to toggle the frequency of the carrier signal according to FSK modulation to encode the communication data. In another example, controller 91 may control polarity switching circuit 94 to switch the polarity of the current signal after a desired portion of the carrier frequency cycle length to shift the phase of the AC current signal by 180 degrees according to BPSK modulation.

Polarity switching circuit 94 is capacitively coupled to the transmitting electrode vector 99 (e.g., electrode 24 and housing 15 in the example shown) via AC coupling capacitor 96. AC coupling capacitor 96 couples the current signal output from polarity switching circuit 94 to the transmitting electrode vector 99 to inject the current into the conductive body tissue pathway. AC coupling capacitor 96 may include one or more capacitors coupled in series with one or each of the electrodes included in electrode vector 99. The AC coupling capacitor 96 is charged to a DC operating voltage at the beginning of a TCC signal. AC coupling capacitor 96 is selected to have a minimum capacitance based on the frequency and the maximum peak-to-peak current amplitude of the carrier signal being used to transmit beacon and data signals. As examples, AC coupling capacitor 96 may have a capacitance of at least one nanofarad up to one microfarad for coupling a carrier signal having a frequency in the range of 25 kHz to 250 kHz and peak-to-peak current amplitude of 100 microamps to 10 milliamps. Larger capacitances may be used but may increase the time required to charge the AC coupling capacitor to a DC operating voltage.

During a "cold start," e.g., at the beginning of a TCC transmission session when AC coupling capacitor 96 is uncharged, the charging of AC coupling capacitor 96 to the DC operating voltage may result in a low frequency current being injected into the body through the transmitting electrode vector. This low frequency current is more likely to interfere with the operation of cardiac event detector 85 or other electrophysiological signal sensing circuits included in co-implanted IMDs or external devices coupled to the patient. Cardiac event detector 85 and other electrophysiological signal sensing circuits of intended or unintended receiving devices may operate in a low frequency band, e.g., 1 to 100 Hz. As such, low frequency artifact at the start of TCC signal transmission, during charging of the AC coupling capacitor 96, may interfere with cardiac event detector 85. After the DC operating voltage is established on AC coupling capacitor 96, the high frequency carrier signal, e.g., 100 kHz, is typically above the operating bandwidth of cardiac event detector 85 and other electrophysiological sensing circuitry of an IMD system and unlikely to cause interference or false event detection.

TCC transmitter 90 may include a voltage holding circuit 98 coupled to AC coupling capacitor 96. Voltage holding circuit 98 is configured to hold the AC coupling capacitor at the DC operating voltage between transmitted TCC signals during a TCC transmission session and/or between TCC transmission sessions. By holding the AC coupling capacitor at a DC voltage during time intervals between TCC signal transmissions, interference with sensing circuitry that may otherwise occur due to the low frequency artifact injected during charging of the AC coupling capacitor 96 to the DC operating voltage is reduced or avoided.

Examples of circuitry included in voltage holding circuit 98 are described in U.S. Patent Application No. 62/591,806 (Peichel, et al.), incorporated herein by reference in its entirety. In some examples voltage holding circuit 98 may include circuitry for floating AC coupling capacitor 96 at the DC voltage between TCC signal transmissions. In other examples, voltage holding circuit 98 may include circuitry to actively hold the AC coupling capacitor 96 at a DC voltage between TCC signal transmissions. A variety of circuitry may be conceived for preventing or minimizing discharging of AC coupling capacitor 96 between TCC signal transmissions. In this way, at the start of transmitting the next TCC signal, the AC coupling capacitor 96 is already at or near the DC operating voltage. Without having to re-establish the DC voltage on the AC coupling capacitor 96, low frequency artifact injected into the TCC tissue pathway at the onset of the next TCC signal transmission is avoided or reduced. It is recognized that leakage currents may still exist within TCC transmitter 90 and may cause some discharge of AC coupling capacitor 96 between signal transmissions. Voltage holding circuit 98 may be used to reduce any discharge of AC coupling capacitor 96 between transmitted TCC signals to reduce low frequency interference with sensing circuit 86 (FIG. 5) of the transmitting device as well as sensing circuits of other co-implanted IMDs and/or external device coupled to the patient.

The TCC transmitter 90 may include protection circuit 97 that allows the delivery of the TCC signal via electrodes coupled to other ICD circuitry but protects the TCC transmitter 90 and other circuitry of the ICD 14 from voltages that may develop across the electrodes, e.g., during a CV/DF shock delivered by therapy circuit 83 or an external defibrillator as well as high voltages that may develop across the TCC transmitting electrode vector during other situations such as an electrocautery procedure or magnetic resonance imaging. The circuitry within housing 15 of ICD 14 protected by protection circuit 97 may include circuitry of any of the components of ICD 14 illustrated in FIG. 5, such as control circuit 80, memory 82, sensing circuit 86, signal generator 84, and RF telemetry circuit 88.

Protection circuit 97 may be coupled between drive signal circuit 92 and the transmitting electrode vector 99, e.g., between AC coupling capacitor 96 and electrode 24 and housing 15 as shown. In some examples, protection circuit 97 may include circuitry before and/or after AC coupling capacitor 96. Protection circuit 97 may include, as examples, capacitors, inductors, switches, resistors, and/or diodes. Examples of TCC signal generation and protection circuitry that may be utilized in conjunction with the signal transmission techniques disclosed herein are generally described in U.S. Pat. No. 9,636,511 (Carney, et al.), incorporated herein by reference in its entirety.

In some examples, TCC transmitter 90 may be controlled by control circuit 80 to transmit data via TCC multiple times throughout a cardiac cycle. In some cases, multiple transmissions at different times during the cardiac cycle increase the likelihood that the data is sent during both systole and diastole to make use of cardiac motion to increase the chance that the intended receiving electrode vector, such as housing-based electrodes of pacemaker 100 or pressure sensor 50, is orientated in a non-orthogonal position relative to the transmitting electrode vector. Multiple transmissions at different times during the cardiac cycle may thereby increase the likelihood that that the packet is received. While TCC transmitter 90 is shown coupled to a transmitting electrode bipole (vector 99) in FIG. 6, it is to be understood that multiple transmitting electrode vectors may be coupled to TCC transmitter 90 for transmitting a TCC current signal along multiple conductive tissue pathways for reception by multiple receiving electrode vectors or to increase the likelihood of being received by a single receiving electrode vector.

Figure 7:
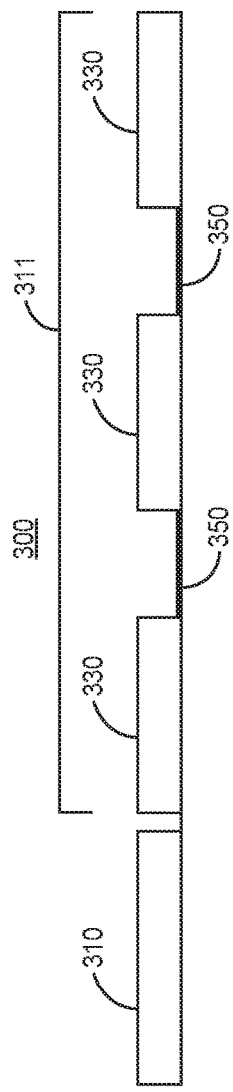
FIG. 7 is a conceptual diagram of a transmission session that may be executed by the TCC transmitter if FIG. 6.

FIG. 7 is a conceptual diagram of a transmission session 300 that may be executed by transmitter 90 under the control of control circuit 80. The challenges of transmitting encoded information in a TCC signal include avoiding unintentional electrical stimulation of nerve and muscle tissue, including myocardial tissue, and avoiding or minimizing interference with sensing circuitry included in one or more devices of the IMD system performing TCC while still successfully transmitting information in a time efficient and power efficient manner. Techniques disclosed herein include a method for transmitting a wakeup signal to a receiving device followed by transmission of encoded data using FSK and/or BPSK modulation of a carrier frequency signal having a frequency and amplitude that is below stimulation thresholds of tissue along the conduction pathway and uses techniques for minimizing interference with sensing circuitry.

Transmission session 300 includes a wakeup mode 310 followed by data transmission mode 311 that may include transmission of one or more data packets 330. In the illustrative examples described herein, a group of bits of encoded data is referred to as a data "packet." In some uses, the term "packet" may imply that transmitted data is guaranteed to be received along a communication pathway without error and a confirmation signal indicating receipt without error may be returned from the intended receiving device. In some applications, a group of bits of encoded data may be referred to as a "datagram" when transmission of the encoded data occurs without guarantee that the data reaches the intended receiver and without certainty that transmission errors did not occur. Groups of bits of encoded data 330 are referred to as "packets" herein, however, it is recognized that in some clinical applications the groups of bits 330 may be transmitted as datagrams, without guarantee that the receiving device actually received the data error-free.

Figure 8:
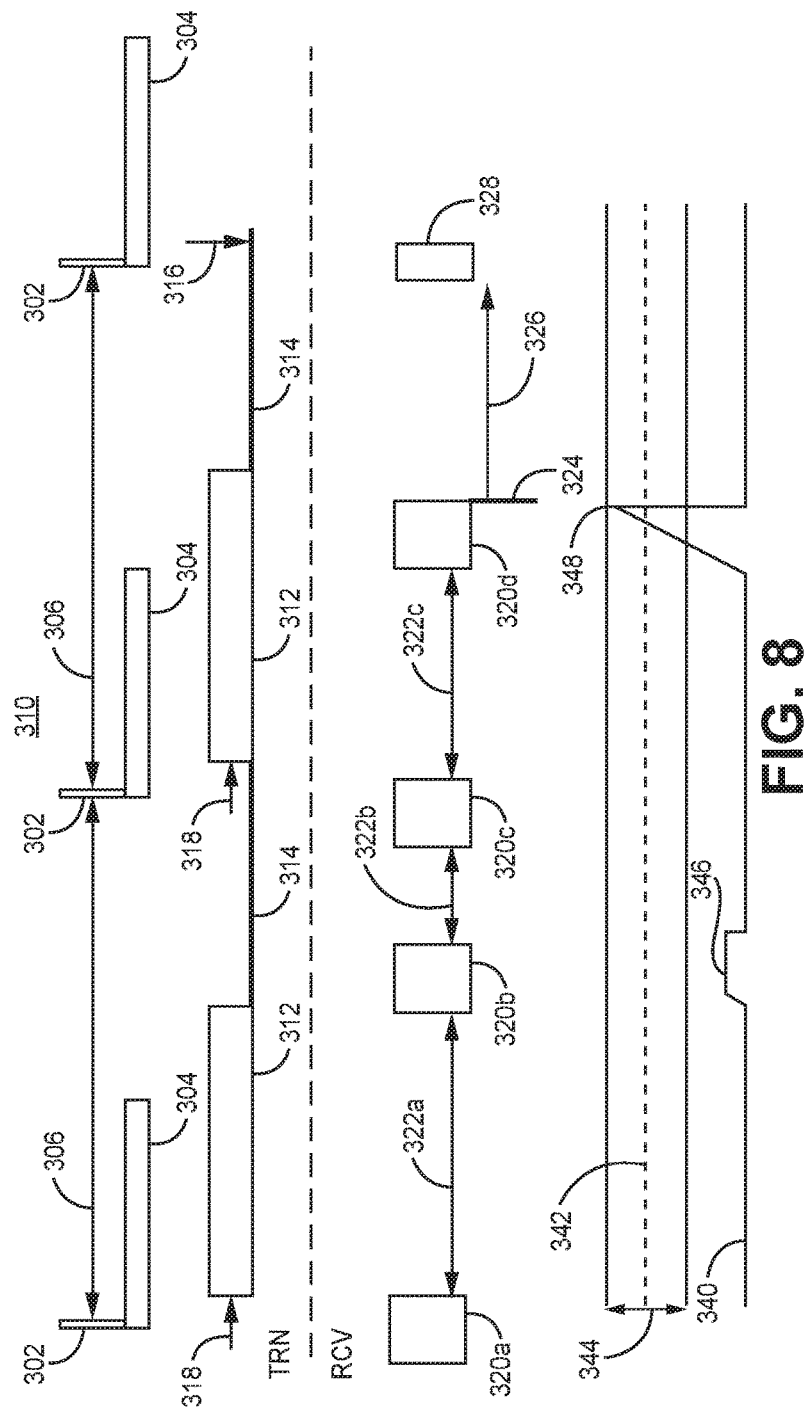
FIG. 8 is a diagram of one example of operations performed during the wakeup mode of the TCC transmitter of FIG. 6 according to one example.

Each transmission session 300 begins with a wakeup mode 310, as further described in conjunction with FIG. 8, followed by at least one data packet 330. Multiple data packets 330 may be transmitted and assembled into a stream of data by the receiving device. In examples that include bi-directional communication, the transmitting device may toggle between data transmission, during which one data packet 330 is transmitted, and a receiving window 350 between data packets, during which the transmitting device waits for a response from the intended receiver, e.g., a signal confirming receipt of the transmitted packet, requested data sent back to the transmitter or other requested response to the received data packet. Examples of the structure of each packet 330 are described below, e.g., in conjunction with FIG. 11.

FIG. 8 is a diagram of one example of operations performed during the wakeup mode 310 by an IMD system, e.g., system 10 of FIG. 1 or system 200 of FIG. 2, according to one example. Functions performed by the transmitting device (TRN) are represented above the dashed line. Functions performed by the receiving device (RCV) are performed below the dashed line. In the example of ICD 14 (or ICD 214) being the transmitting device, control circuit 80 controls TCC transmitter 90 to transmit a beacon signal 312 to wake up the receiving device. In the example of pacemaker 100 being the receiving device, control circuit 170 may power up TCC signal detector 175 (shown in FIG. 3B) periodically for a beacon search period 320 (multiple beacon search periods 320a-d are shown in FIG. 8) to determine if the beacon signal is detected.

In some examples, the beacon signal 312 may be transmitted multiple times as needed until a response is received from the receiving device. In the example shown, the beacon signal 312 is sent twice, each time followed by a receiving period 314 for waiting for acknowledgement signal 328 transmitted from the receiving device to confirm detection of the beacon signal 312. In response to receiving the acknowledgement signal 328 as indicated at arrow 316, the transmitter 90 stops transmission of the beacon signal 312 and switches from the wakeup mode 310 to the transmission mode 311 as shown in FIG. 7.

If the transmitting device includes a sensing circuit, such as sensing circuit 86, at least the first beacon signal 312 may be started during a blanking period 304 applied to the sensing circuit 86 following a cardiac event 302. At the start of a transmission session, the early cycles of the carrier frequency signal establish a DC voltage across the AC coupling capacitor 96. During this time, which may be 10 ms, 50 ms, 100 ms, or even up to 200 ms or more, a low frequency current may be injected into the body tissue conductive pathway via the TCC transmitting electrode vector. The low frequency current is more likely to cause interference with cardiac event detector 85 of sensing circuit 86 (or other electrical signal sensing circuits of other implanted devices) than the relatively high carrier frequency of the TCC signal. By starting the transmission session during a blanking period 304 applied to the sensing circuit 86 of the transmitting device, the DC voltage is established on the AC coupling capacitor 96 mostly or entirely during the blanking period 304 when the cardiac event detector 85 is blanked and relatively immune to the low frequency artifact.

The blanking period 304 may be an automatic blanking period that the control circuit 80 applies to the cardiac event detector 85 following an intrinsic or paced cardiac event 302. Cardiac event 302 may be an intrinsic cardiac event sensed by the cardiac event detector 85, and blanking period 304 may be a post-sense blanking period set in response to detecting the intrinsic cardiac event, e.g., an R-wave or P-wave. For example, a post-sense blanking period may be applied to a sense amplifier or other cardiac event detection circuitry of sensing circuit 86 in response to a cardiac event sensing threshold crossing. At other times, cardiac events 302 may be pacing pulses delivered at a pacing interval 306, in which case blanking period 304 is a post-pace blanking period automatically applied to the sensing circuit 86 upon delivery of the pacing pulse by therapy circuit 83. A post-pace or post-shock blanking period may be applied to prevent saturation of the sense amplifier(s) of sensing circuit 86 during delivery of a pacing pulse or cardioversion/defibrillation shock. An automatic post-sense or post-pace blanking period may be in the range of 50 to 200 ms, for example 150 ms.

Low frequency current injected into body tissue at the beginning of a TCC signal transmission, such as beacon signal 312, as the AC coupling capacitor 96 is charged to a DC operating voltage is not detected as a cardiac event by cardiac event detector 85 during a blanking period 304. Furthermore, during a post-sense, post-pace or post-shock blanking period, myocardial tissue is in a state of physiological refractoriness such that any low frequency signal injected at the beginning of a TCC signal started during a blanking period 304 is highly unlikely to capture the myocardial tissue.

In the example of the receiving device being pacemaker 100 having sensing circuit 174, control circuit 170 may apply a post-sense or post-pace blanking period in response to detecting an intrinsic cardiac event or delivering a pacing pulse. The blanking period applied to sensing circuit 174 by control circuit 170 is applied to cardiac event detector 173 to prevent oversensing of non-cardiac events during the blanking period. The blanking period is not applied to TCC signal detector 175, which may be operating in a polling mode including beacon search periods 320 and enabled to detect a beacon signal, even during a blanking period applied to cardiac event detector 173. Since both pacemaker 100 and ICD 14 (or ICD 214) may be configured to sense cardiac electrical signals from heart 8, and may be configured to detect pacing pulses delivered by another co-implanted device, both sensing circuits 86 and 174 of the transmitting and receiving devices, respectively, may be in a blanking period at the same time or at least during overlapping time periods. As such, by starting transmission of at least the first beacon signal 312 of a new transmission session during a blanking period 304, sensing circuitry of other co-implanted devices configured to detect cardiac electrical signals may also be in a blanking period, reducing the likelihood of low frequency interference with cardiac event detection by other sensing circuits during AC coupling capacitor charging.

In the example shown, control circuit 80 may control transmitter 90 to transmit each beacon signal 312 to be started during a blanking period 304. In other examples, only the first beacon signal 312 is started during the blanking period 304 and other techniques may be used to avoid or reduce interference at the start of any subsequent beacon signals. For example, voltage holding circuit 98 may be controlled by controller 91 to float or actively hold AC coupling capacitor 96 at the DC voltage that was established during the first beacon signal 312 during the receiving period 314. At the start of the next beacon signal 312, the AC coupling capacitor 96 is already at (or near) the DC operating voltage such that low frequency artifact during the early cycles of the carrier frequency is reduced or avoided. Only the first beacon signal 312 may be required to be started during a blanking period 304, and transmission of any subsequent beacon signals 312 is not limited to the timing of cardiac events 302 and blanking periods 304.

In other examples, every beacon signal 312 is started during a blanking period 304. In this case, control circuit 80 identifies a cardiac event 302, applies a blanking period 304, and controls the transmitter 90 to start the beacon signal 312 during the blanking period. The beacon signal 312 is shown to extend later in time than blanking period 304. In some examples, the beacon signal 312 may be started after a delay interval 318 from the start of the blanking period 304. In other examples, beacon signal 312 may start at the beginning of blanking period 304 and may have a duration that is less than, equal to or greater than blanking period 304. The TCC signal detector 175 of the receiving device may be blinded to a TCC signal during and immediately following delivery of a therapeutic stimulation pulse, e.g., a pacing pulse, due to saturation of an amplifier in the TCC signal detector 175. As such, transmitter 90 may be controlled to transmit the beacon signal 312 for a time period that extends outside blanking period 304 to increase the likelihood of detection by a receiving device outside of a period of amplifier saturation.

Control circuit 80 may alternatively apply a communication blanking period to cardiac event detector 85 that is independent of the timing of cardiac electrical events, sensed or paced. In some cases, a communication blanking period may be applied during the cardiac cycle between sensed or paced events. The communication blanking period may be applied by control circuit 80 to the cardiac event detector 85 to enable TCC signal transmission to be initiated at any time during the cardiac cycle, without waiting for an automatic post-sense or post-pace blanking period.

A communication blanking period may be shorter or longer than the automatic post-sense or post-pace blanking period. For example, a communication blanking period may be in the range of 10 ms to 200 ms and may depend on the programmed sensitivity of the cardiac event detector 85 and the duration of low frequency interference expected at the start of the beacon signal transmission. The maximum duration of the communication blanking period may be limited based on the particular clinical application. For example, in the cardiac monitoring and therapy delivery IMD systems 10 and 200 disclosed herein, the maximum time that cardiac event detector 85 is blinded to detecting cardiac events may be 200 ms or less. In non-cardiac applications, e.g., monitoring muscle or nerve signals, longer or shorter communication blanking intervals may be applied.

In some examples, the beacon signal 312 may include a single tone at the unmodulated carrier signal frequency, e.g., 100 kHz and may be transmitted for 100 ms, 200 ms, 500 ms, 1 second, 2 seconds, or even up to 8 seconds. As described below, in other examples the beacon signal 312 may vary between two or more tones within a range of the carrier signal. For instance, the beacon signal 312 may be an FSK signal modulated between two different frequencies to transmit beacon signal 312 having a pre-defined frequency signature that is detected by the TCC signal detector 175 of the receiving device, e.g., pacemaker 100 or pressure sensor 50. In this manner, the property of the carrier signal being modulated is the frequency.

The TCC signal detector 175 of the receiving device is configured to detect the beacon signal frequency and compare the frequency to detection criteria. The TCC signal detector 175 may include a comparator and counter configured to count pulses, e.g., by counting zero crossings, edges or other features of the voltage signal received at the receiving electrode vector, and comparing the count to a beacon detection threshold value. In other examples, the TCC signal detector 175 of the receiving device may include a phase locked loop (PLL) that detects the frequency of the voltage signal at the receiving electrode vector. The frequency signal output of the PLL may be compared to the expected beacon signal frequency or frequency pattern.

The peak-to-peak amplitude of the carrier signal transmitted as a beacon signal 312 may be increased compared to the peak-to-peak amplitude of the carrier signal during data packets 330. The greater peak-to-peak amplitude of the beacon signal 312 may increase the likelihood of the beacon signal 312 being detected by the receiving device. In other examples, the peak-to-peak amplitude of the carrier signal transmitted during beacon signal 312 is the same as the peak-to-peak amplitude of the modulated carrier signal during data packet transmission.

In the example of FIG. 8, the receiving device includes a counter for determining a pulse count 340 during a beacon search period 320. The TCC signal detector 175 may be configured to count voltage pulses received at the receiving electrode vector and compare the value of a pulse count to a beacon detection threshold 342 or threshold range 344. A single count may correspond to one detected cycle of an assumed carrier signal (one positive and one negative polarity pulse each having a half cycle width). The beacon detection threshold 342 and threshold range 344 may be defined based on the known, unmodulated carrier signal frequency of beacon signal 312 for the example of the single tone, carrier frequency beacon signal. The threshold 342 may be set to a percentage of the number of cycles of the carrier signal frequency expected during a predetermined time interval, e.g., 40%, 50%, 60%, 70%, or up to 100% of the expected number of pulses.

The beacon detection threshold range 344 may be defined by a maximum and minimum greater than and less than the detection threshold 342, respectively. The beacon detection threshold range 344 may be centered on detection threshold 342 and defined as a percentage of the detection threshold, e.g., ±6.25%, ±12.5%, ±25%, ±50% or other predetermined percentage of the detection threshold 342. The TCC signal detector 175 of the receiving device may detect the beacon signal 312 in response to a pulse count in the threshold range 344. Pulse counts lower than the threshold range 344 may be associated with baseline noise or other non-TCC signals. Pulse counts greater than the threshold range 344 may be associated with electromagnetic interference (EMI) or other high frequency noise that the patient may be subjected to.

The predetermined time interval that the beacon detection threshold 342 and range 344 are based on may be equal to the duration of each of the beacon search periods 320. In other examples, the predetermined time interval that detection threshold 342 is based on may be a portion of a beacon search period 320 (i.e., less than the duration of each beacon search period 320a-d). If the beacon signal 312 starts or ends during a beacon search period 320, the TCC signal detector 175 of the receiving device may still detect beacon signal 312 if there is enough overlap of the beacon signal 312 and a beacon search period 320 to allow the pulse count 340 to reach the detection threshold range 344 during a beacon search period 320.

For example, if the carrier frequency is 100 kHz and the beacon search period is 4 ms long, up to 400 carrier frequency cycles may occur during the beacon search period. The detection threshold 342 may be a count of at least 320 carrier frequency cycles, and the range 344 may be ±25% or 240 to 400 cycles. A beacon signal 312 overlapping with at least 60% of the beacon search period 320 may be detected. In other examples, the beacon detection threshold may be set to a value equal to the expected count of carrier frequency cycles if the beacon signal 312 is transmitted continuously over the entire duration of the beacon search period 320. Using the example given above, the threshold 342 may be a count of 400 with a range that allows for ±10 to 20% error.

The duration of the beacon signal 312 is shown to be longer than the duration of each of the beacon search periods 320a-d in the example of FIG. 8. The duration of the beacon signal 312, however, may be less than, equal to or greater than a beacon search period 320 in various examples. For instance, with no limitation intended, the beacon signal 312 may be approximately 8 ms to 150 ms long. The beacon search period 320 may be 0.4 to 4 ms long. In other examples, the beacon signal 312 may be up to one second long, up to four seconds long, or even up to eight seconds long. The beacon signal transmission may be suspended if a therapy such as a pacing pulse is scheduled for delivery, e.g., by therapy circuit 83. Transmission of a suspended beacon signal may be resumed after delivery of the pacing pulse. The beacon search period may be any portion of the beacon signal.

The receiving device controls the TCC signal detector, e.g., TCC signal detector 175 of FIG. 3, to operate in a polling mode until a beacon signal is detected. The polling mode includes beacon search periods 320a-d separated by polling intervals 322a-c. The polling intervals 322a-c are shown as variable intervals in FIG. 8. Polling intervals 322a-c may be random or pseudo-random intervals, e.g., selected from a limited range of polling intervals. Polling intervals 322a-c may be randomly or pseudo-randomly selected over a range of 5 ms to 1 second, a range of 8 ms to 200 ms, or a range of 8 ms to 120 ms, as examples. In other examples, polling intervals 322a-c may vary or alternate between two, three, or more fixed polling interval durations, e.g., 100 ms, 750 ms, and 2 seconds. In still other examples, polling intervals 322a-c may be equal to each other, set to a fixed, pre-determined value, e.g., from 0.5 seconds to 8 seconds.

In some instances, a fixed polling interval may unintentionally track or approximately track a cardiac pacing rate. For example, at a pacing rate of 60 paces per minute, a polling rate of once per second may coincidentally result in beacon search periods 320 being scheduled simultaneously with a pacing pulse being delivered, when the sensing circuit of the receiving device is blanked or blinded due to amplifier saturation, e.g., when TCC signal detector 175 of pacemaker 100 is blinded during a pacing pulse being delivered by pulse generator 176 or by ICD 14 or 214. Detection of the beacon signal 312 may fail or require an unacceptably long time for detection. By using variable polling intervals, as represented by polling intervals 322a-c, the TCC signal detector 175 of the receiving device is expected to be enabled to detect the beacon signal at times that do not coincide with a delivered pacing pulse or intrinsic heart beat at least some of the time during the wakeup mode 310. As such, the TCC signal detector 175 may be configured to operate in a polling mode during which TCC signal detector 175 sets polling intervals 322a-c to multiple, randomly selected polling interval durations.

In FIG. 8, the first, earliest beacon search period 320a occurs just before the first beacon signal 312 of wakeup mode 310, when no beacon signal is being transmitted. The pulse count 340 remains at a low level, which may be non-zero due to baseline noise but below the beacon detection threshold range 344. The second beacon search period 320b overlaps a portion of the beacon signal 312. The pulse count 340 increases to a subthreshold value 346 during beacon search period 320b but stops increasing at the end of the beacon signal 312 and does not reach the detection threshold range 344.

The third beacon search period 320c occurs during the receiving period 314 of transmitter 90. The fourth beacon search period 320d occurs during beacon signal 312. The pulse count 340 reaches peak value 348 that is within the beacon detection range 344, without exceeding the maximum of the detection range 344. The receiving device TCC signal detector 175 may generate a beacon detection interrupt signal 324 that is passed to the control circuit of the receiving device, e.g., control circuit 170 of pacemaker 100. The control circuit may end the polling mode of the receiving device and switch to a communication receiving mode to enable reception of data packets 330 by the TCC signal detector 175. During the communication receiving mode, the TCC signal detector 175 is powered up (woken up) to receive TCC signals until the TCC transmission session is complete.

In the example shown, the receiving device may include a TCC transmitter 175 that is controlled to transmit an acknowledgement signal 328 back to the transmitting device to confirm beacon signal detection and that the receiving device is waiting to receive data packet transmissions. The acknowledgement signal 328 may be transmitted after a delay period 326 to ensure that the transmitting device is no longer transmitting the beacon signal 312 and has switched to a receiving period 314 and is capable of receiving the acknowledgement signal.

The transmitting device enables TCC receiver 87 to detect an acknowledgement signal 328, e.g., by powering the TCC receiver 87 to enable the various filters, amplifiers, comparators, phase locked loops, or other circuitry to receive and detect the acknowledgement signal 328. TCC receiver 87 may generate an acknowledgement detect signal 316 passed to control circuit 80. Control circuit 80 switches the transmitting device from the wakeup mode 310 to a data transmission mode 311 during which the data packets 330 are transmitted.

In other examples, beacon signal 312 may be transmitted multiple times during a cardiac cycle or over more than one cardiac cycle. The beacon signal 312 may be followed by an OPEN command signal transmitted to the receiving device. The receiving device may detect the beacon signal and switch to a data receiving mode. Upon receiving the subsequent OPEN command signal, the receiving device may transmit an acknowledgement signal back to the transmitting device to confirm to the transmitting device that the TCC signal detector 175 is powered on and ready to receive data transmissions.

Figure 9:
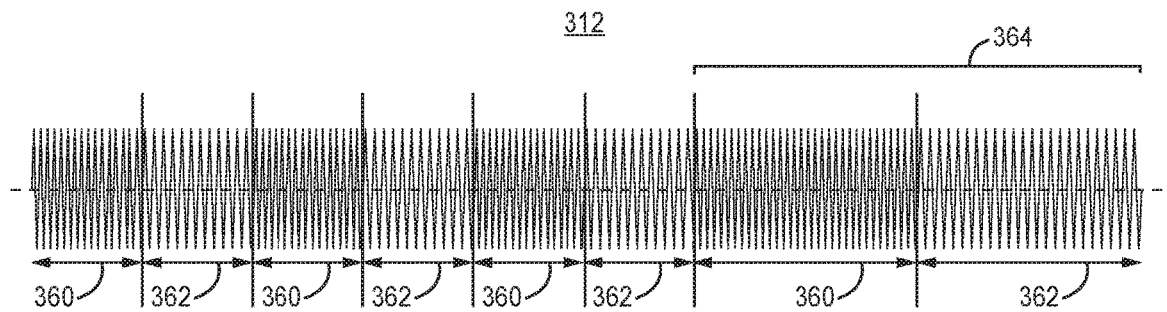
FIG. 9 is a diagram of beacon signal that may be generated by the TCC transmitter of FIG. 6 according to one example.

FIG. 9 is a diagram of beacon signal 312 according to one example. A single tone beacon signal, e.g., transmitted at the carrier signal frequency, may result in false beacon signal detections and wakeups by the receiving device. A TCC signal detector configured to detect a single tone beacon signal, e.g., at the carrier signal frequency, may make false beacon signal detections at an unacceptably high rate. EMI or baseline noise may cause false beacon signal detections when no beacon signal is being transmitted. False wakeups unnecessarily use battery power of the receiving device. In order to avoid false wakeups, transmitter 90 may be controlled to transmit an FSK modulated beacon signal. An FSK modulated beacon signal may be discriminated from other single-tone noise or EMI that the receiving device may be subjected to.

The beacon signal 312 shown in FIG. 9 is an FSK modulated beacon signal that alternates between a high frequency 360 and a low frequency 362 and is terminated by an end-of-beacon signature 364 that is distinct from the preceding alternating intervals of high frequency 360 and low frequency 362. In the example of a 100 kHz carrier signal frequency, the high frequency 360 may be in the range of 102 kHz to 120 kHz, and the low frequency 362 may be in the range of 85 to 98 kHz. For example, the beacon signal may alternate between 98 kHz and 102 kHz, 95 kHz and 105 kHz, or 92 kHz and 108 kHz.

Keeping the high and low frequencies within a bandpass filter range of the carrier signal frequency may enable the TCC signal detector 175 to use a common bandpass filter for detecting the FSK modulated beacon signal and a BPSK modulated carrier signal transmitted as a data packet or datagram. In another example, the FSK modulated beacon signal 312 alternates between a low frequency 362 of 85 kHz and a high frequency 360 of 115 kHz.

The beacon signal 312 may be transmitted with alternating fixed numbers of cycles at each high and low frequency 360 and 362, e.g., 8 cycles, 12 cycles, 16 cycles, 24 cycles, 32 cycles or more. The number of cycles transmitted at each frequency may be selected so that each high and low frequency 360 and 362 is transmitted for the same time interval to facilitate detection of at least one or both of the two different frequencies over the expected time interval by the TCC signal detector 175. In one example, the high frequency 360 is eight-sevenths of the carrier signal frequency, and the low frequency 362 is three-fourths of the high frequency 360. In this example using a 100 kHz carrier signal, the high frequency 360 is 115 kHz, and the low frequency is 85 kHz. The high frequency 360 may be delivered for 16 cycles, and the low frequency 362 may be delivered for 12 cycles so that each frequency is delivered for equal, 140 microsecond time intervals.

In still other examples, the high and low frequencies 360 and 362 may be selected to be different than a range that includes the carrier signal frequency being used for data packet transmission. The high and low frequencies 360 and 362 of the FSK modulated beacon signal 312 may both be higher or both lower than the carrier signal frequency used during data transmission rather than one higher and one lower than the carrier signal frequency used during the data transmission mode. As an example, the carrier signal frequency during transmission of data packets 330 shown in FIG. 7 may be 100 kHz, and the high and low frequencies 360 and 362 may be 150 and 200 kHz, respectively.

The receiving device may be configured to poll for the beacon signal using relatively short and/or infrequent beacon search periods to conserve power. The beacon signal 312 may be transmitted for a relatively long time interval, e.g., up to one second or more, in order to increase the likelihood of being detected by the receiving device. The relative orientation of the transmitting and receiving electrode vectors may vary over a cardiac cycle and over a respiration cycle. As a result, the voltage signal amplitude at the receiving electrode vector may vary over time during a relatively long beacon signal and may even drop out due to positional changes of the transmitting and receiving electrode vectors caused by cardiac, respiratory or other body motion.

A long beacon signal, e.g., 1 second or more or even 0.5 seconds or more, may also interfere with pacing pulse delivery. If the therapy circuit 83 is scheduled to deliver a pacing pulse during a beacon signal, the beacon signal is suspended to allow pacing pulse delivery. The receiving device sensing circuit may be blinded due to the large amplitude pacing pulse causing polarization artifact on the receiving electrode vector. In the case of ICD 214 being the transmitting device, dual-chamber pacing or multi-chamber CRT may be delivered by ICD 214 resulting in two, three or even four pacing pulses per cardiac cycle.

In order to avoid signal drop out and avoid competition between beacon signal transmission and pacing pulse delivery, the beacon signal 312 may be delivered over a short time interval that is less than the cardiac cycle or less than the respiratory cycle (depending on the implant locations and body motion that may be contributing to signal drop out). For example, the beacon signal 312 may be transmitted for 200 ms, 150 ms, 120 ms, 100 ms or less. In some examples, the beacon signal 312 is between 8 ms and 118 ms. The beacon signal 312 may be transmitted multiple times during a single cardiac cycle to promote transmission at a time that the transmitting and receiving electrode vectors are in optimal alignment (or at least avoid times that the receiving vector is orthogonal to the current pathway).

The receiving device may be configured to detect the beacon signal based on positively detecting one or both of the high and low frequencies 360 and 362. For instance, the receiving device may be configured to detect either the high frequency 360 or the low frequency 362 for the expected number of cycles separated by time intervals equal to the expected number of cycles that the same frequency is not detected. Alternatively, the receiving device may be configured to positively detect both the high and low frequencies 360 and 362 for the expected number of cycles (and equal time intervals) of each frequency in the alternating FSK pattern. For example, TCC signal detector 175 may be configured to determine a cycle count over predetermined time intervals and when the cycle count alternates a predetermined number of times between two different beacon detection threshold ranges uniquely defined for the respective high and low frequencies 360 and 362, the beacon signal is detected. In another example, the TCC signal detector 175 includes a PLL that detects the alternating high and low frequencies 360 and 362.

To promote appropriate timing of waking up the receiving device and avoid false wakeups, the beacon signal 312 may be terminated with an end-of-beacon signature 364. The end-of-beacon signature 364 may include any combination of high frequency 360 and/or low frequency 362 intervals. It is recognized that numerous variations of an end-of-beacon signature may be used that includes a distinct number of cycles of the high frequency 360 and/or the low frequency 362 that is different than the number of cycles of each respective frequency delivered during the FSK modulated beacon signal 312 leading up to the end-of-beacon signature 364. In one example, each of the high frequency 360 and the low frequency 362 may be delivered for twice the number of cycles during the end-of-beacon signature compared to prior to the end of beacon signature. In the example given above including 16 cycles of high frequency 360 alternating with 12 cycles of low frequency 362, the end-of-beacon signature may include 32 cycles of the high frequency 360 alternating with 24 cycles of the low frequency 362.

While shown with only one pair of alternating high and low frequencies 360 and 362 for the sake of illustration, it is to be understood that the end-of-beacon signature 364 may include multiple sequential pairs of high and low frequency intervals, for example eight sequential pairs. In this example, using the high and low frequencies of 115 kHz and 85 kHz given above, the end-of-beacon signature may be 56 ms in duration. Similarly, while only three pairs of alternating high and low frequency intervals prior to the end-of-beacon signature 364 are shown for the sake of illustrating beacon signal 312 in FIG. 9, the number of paired alternating high and low frequency intervals that precede the end-of-beacon signature 364 may be selected in order to achieve a desired beacon signal duration. The total duration of beacon signal 312 may be 50 ms to 1000 ms. In some examples, the total beacon signal duration is 120 ms or less including an end-of-beacon signature that is 60 ms or less.

The receiving device may discriminate between beacon signal drop out and the true end of the beacon signal 312 by positively detecting the end-of-beacon signature 364 as opposed to the alternating predetermined number of cycles of the FSK high and low frequencies 360 and 362 preceding the end-of-beacon signature just dropping out. If the alternating high and low frequencies 360 and 362 are detected but the end-of-beacon signature 364 is not detected, the beacon signal 312 may not be detected by the receiving device. The receiving device remains in the polling mode. If the end-of-beacon signature 364 is detected, the receiving device switches to a data receiving mode and may transmit an acknowledgement signal to the transmitting device to indicate that the TCC signal detector 175 is powered up and ready to receive data packets.

Figure 10:
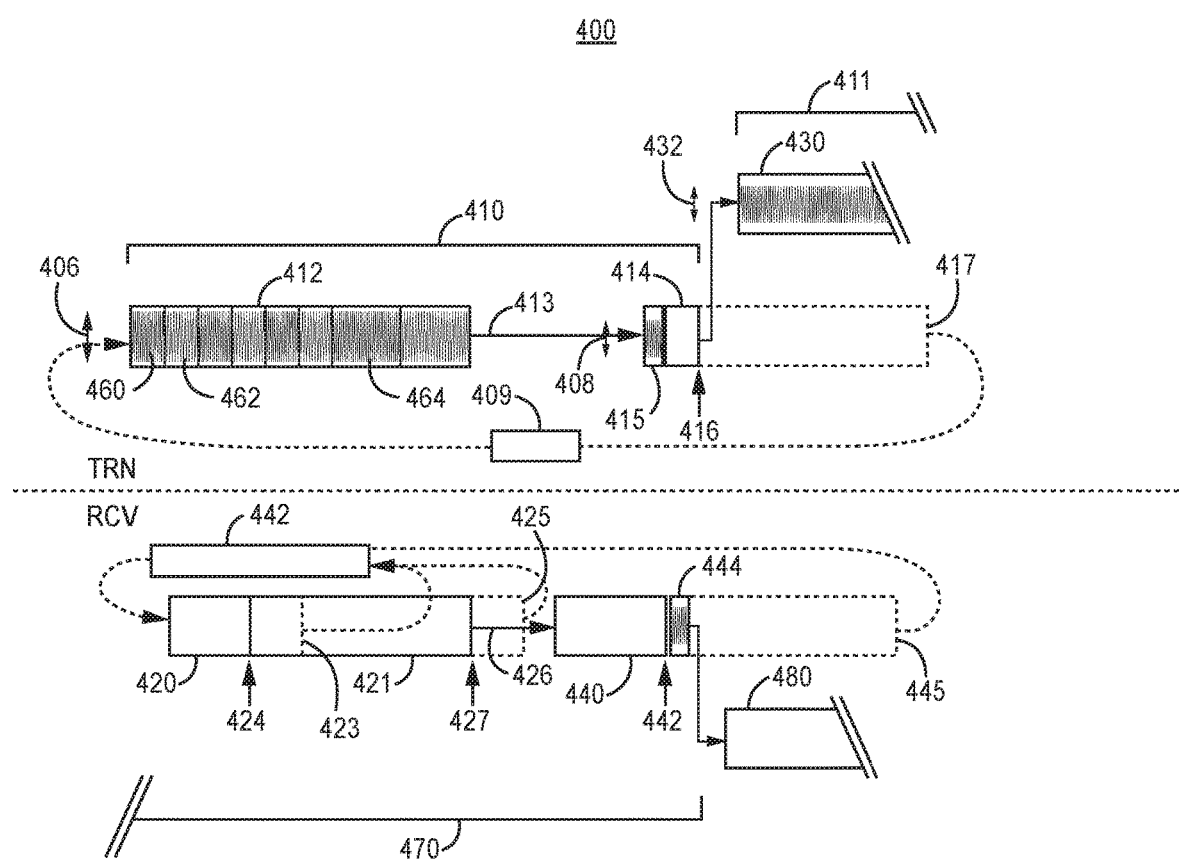
FIG. 10 is a diagram of a portion of a transmission session performed by an IMD system, such as the system of FIG. 1 or the system of FIG. 2, according to one example.

FIG. 10 is a diagram of a portion of a transmission session 400 performed by an IMD system, such as system 10 of FIG. 1 or system 200 of FIG. 2, according to one example. The transmitting device (TRN) operations are depicted above the dashed line, and the receiving device (RCV) operations are depicted below the dashed line. The transmitting device operates in a wake-up mode 410 and a data transmission mode 411. The receiving device operates in a polling mode 470 and a data receiving mode 480.

The control circuit 80 of the transmitting device, e.g., ICD 14 or ICD 214, may determine that a TCC transmission session 400 is pending and enable the TCC transmitter 90 to operate in the wake-up mode 410. The control circuit of the receiving device, e.g., pacemaker 100 or pressure sensor 50, controls the TCC signal detector 175 to operate in the polling mode 470 by starting a beacon search period 420 after a polling interval 422 according to a polling schedule. The polling schedule may be based on a fixed polling interval 422 or include variable, random, or pseudo-random polling intervals as described above. In some examples, the polling mode 470 is enabled for designated time periods in the day, e.g., only at night, every 4 hours, every 8 hours, every 24 hours or other predetermined time intervals.

The TCC signal detector 175 may be controlled to set beacon search periods 420 at one frequency during one time interval and at a second frequency different than the first frequency during a second time interval. For example, ICD 214 may transmit TCC signals to pressure sensor 50 during the night, when a patient is asleep. Pressure sensor 50 may be configured to operate in the polling mode 470 by scheduling beacon search periods more frequently during the night than during the day. The polling interval 422 may still be variable, random or pseudo-random, but may have a shorter average interval duration during the night than during the day so that the average polling frequency is higher at night. In other examples, the receiving device may operate in the polling mode 470 only during the night, or other pre-determined time period, and TCC signal reception may be disabled during other times. As such, polling mode 470 may operate continuously from the end of a completed transmission session until a beacon signal is detected or operate discontinuously between transmission sessions.

In another example, if pacemaker 100 is the receiving device, pacing or other therapy may be expected more frequently during the day when the patient is awake and active. ICD 14 of system 10 may be configured to transmit data to pacemaker 100 to confirm rhythm detection and/or coordinate therapy delivery more often during the day than during the night. As such, pacemaker 100 may be configured to operate according to one polling schedule that sets relatively shorter polling intervals during the day and a second polling schedule that sets relatively longer polling intervals during the night. Variable or randomly set polling intervals may have overlapping values during the day and night time periods in some instances, but an average polling frequency during the first time period, e.g., during the day, may be greater than the average polling frequency during the second time period, e.g., during the night. In this example, polling mode 470 may be continuous between data receiving modes 480 but may operate according to two or more different average polling frequencies between a preceding data receiving mode and the next data receiving mode 480.

The transmitting device transmits a beacon signal 412, which may be an FSK modulated beacon signal alternating between a high frequency 460 and a low frequency 462 as described in conjunction with FIG. 9. Beacon signal 412 may be transmitted having a peak-to-peak amplitude 406 that may be greater than a peak-to-peak amplitude 432 of the carrier signal during the data transmission mode 411. The beacon signal 412 may be terminated with an end-of-beacon signature 464 as described above.

TCC transmitter 90 is configured to wait for a post-beacon interval 413 after beacon signal 412 before transmitting an OPEN command 415. The post-beacon interval 413 is provided to allow time for the receiving device to detect the beacon frequency pattern of alternating intervals of high and low frequencies 460 and 462, detect the end-of-beacon signature 464, and start searching for the OPEN command 415. The beacon signal 412 may be 100 ms to 1 second in duration followed by a post-beacon interval 413, which may be between 100 ms and 200 ms. In some examples, the beacon signal 412 may be transmitted repeatedly, e.g., two or more times during a cardiac cycle, before waiting the post-beacon interval 413 and transmitting the OPEN command to increase the likelihood of the beacon signal being detected by the receiving device. Relatively short beacon signals, e.g., 8 to 100 ms, may be repeated at multiple times during the cardiac cycle to promote transmission at a time that the receiving electrode vector is parallel to the tissue conductance pathway of the injected current.

The OPEN command 415 may be 1 ms to 25 ms, e.g., 8 ms in duration. The OPEN command 415 may be transmitted as the single-tone carrier frequency, e.g., a 100 kHz signal, for a predetermined duration, e.g., 8 ms. The OPEN command 415 may have a peak-to-peak amplitude 408 that is the less than the peak-to-peak amplitude 406 of the beacon signal in some examples. The higher peak-to-peak amplitude 406 may be transmitted to promote beacon signal detection by the receiving device. A reduced amplitude OPEN command 415 may be reliably detected by the receiving device that has been woken up by the beacon signal 412.

During the polling mode 470, the receiving device starts a beacon search period 420 during which the TCC signal detector 175 operates to detect the alternating frequency pattern of FSK modulated beacon signal 412. In the examples given above, in which each frequency 460 and 462 are transmitted for 140 microsecond intervals in an alternating pattern, the TCC signal detector 175 may detect the beacon frequency pattern within as little as 5 ms or less. The beacon search period 420 may have a maximum duration extending to end time 423. If the beacon frequency pattern is not detected within the beacon search period 420, before end time 423, the receiving device control circuit may power down the TCC signal detector 175 for the next polling interval 422 (as indicated by the curved dashed arrow), until the next beacon search period 420 in accordance with the polling schedule.

If the beacon frequency pattern is detected during the beacon search period 420 (before end time 432), the TCC signal detector 175 is controlled to track the frequency of the beacon signal during a beacon tracking period 421. In the example of FIG. 10, the alternating high and low frequencies 460 and 462 are detected at arrow 424 during beacon search period 420, and the beacon tracking period begins without waiting for the beacon search period end time 423. Once the beacon frequency pattern is detected, The TCC signal detector 175 tracks the pairs of alternating signal frequencies during beacon tracking period 421 to search for the end-of-beacon signature 464.

The beacon tracking period 421 may have a maximum time limit extending to beacon tracking period end time 425. If the end-of-beacon signature 464 is not detected within the maximum beacon tracking period 421 after detecting the beacon frequency pattern at arrow 424, beacon signal drop out may be detected. The beacon signal 412 is not detected, and the TCC signal detector 175 may be powered down for the next polling interval 422 according to the polling schedule (as indicated by dashed arrow).

In the example of FIG. 10, the end-of-beacon signature 464 is detected at arrow 427 during beacon tracking period 421. In response to positively detecting the end-of-beacon signature 464, the TCC signal detector 175 may pass a beacon detect signal 427 to the control circuit of the receiving device. In response to the beacon detect signal 427, the control circuit controls the TCC signal detector 175 to terminate the beacon tracking period 421 and may start a post-detection delay interval 426. After the delay interval 426, the TCC signal detector 175 is enabled to receive the OPEN command 415 during an OPEN search window 440. The OPEN search window 440 may be started after a delay interval 426 that is 100 ms or less, for example. The delay interval 426 may be provided to allow the TCC transmitter 90 to complete beacon transmission and switch to transmission of the OPEN command 415 after the post-beacon interval 413. In other examples, the TCC signal detector 175 is enabled to detect the OPEN command 415 in response to the beacon detect signal 427 without delay interval 426.

The OPEN search window 440 may be up to 250 ms long before timing out at the end time 445 of OPEN search window 440. If OPEN search window 440 expires at end time 445 without detecting the OPEN command 415, TCC signal detector 175 is powered down for a polling interval 422 until the next beacon search window 420 in accordance with the polling schedule.

In the example shown, the OPEN command 415 is detected by TCC signal detector 175 during the OPEN search window 440. An OPEN detect signal 442 is generated by the TCC signal detector 175 and passed to the control circuit of the receiving device. The control circuit controls a TCC signal transmitter, if included in the receiving device, to transmit an acknowledgement signal 444. The acknowledgement signal 444 may be transmitted within 20 ms, e.g., within 2 to 3 ms, of detecting the OPEN command 415. The acknowledgement signal 444 may be transmitted at the carrier frequency for up to 25 ms and is transmitted for 7 ms in one example.

After transmitting the acknowledgement signal 444, the control circuit of the receiving device switches the TCC signal detector 175 to the data receiving mode 480. In some examples, the receiving device may not be configured to transmit TCC signals and may switch from the OPEN search window 440 to the data receiving mode 480 without transmitting acknowledgement signal 444. During the data receiving mode, the TCC signal detector 175 detects transmitted data packets, as described below. Detection of the data packets may include detecting phase shifts of the carrier frequency to demodulate the BPSK modulated carrier frequency and produce a bit stream that is passed to the receiving device control circuit for decoding. As such, the transition from the polling mode 470 to the data receiving mode 480 may include switching from detecting and demodulating an FSK modulated beacon signal to detecting and demodulating a BPSK modulated data packet.

The transmitting device controls TCC receiver 87 to search for the acknowledgement signal 444 during an acknowledgment receiving period 414. Acknowledgment receiving period 414 may have a maximum duration for waiting for the acknowledgment signal 444. If the acknowledgement signal 444 is not detected by the transmitting device by the end time 417 of the acknowledgment receiving period 414, the control circuit 80 of the transmitting device remains in the wakeup mode 410 by waiting for a beacon control interval 409 and re-transmitting the beacon signal 412, as indicated by the dashed arrow. If a maximum number of beacon signals 412 are transmitted without receiving an acknowledgement signal from the intended receiving device, the transmitter 90 may be controlled to increase the peak-to-peak amplitude 406 of the beacon signal 412 and/or adjust the beacon control interval 409 (e.g., to a longer or shorter interval) to alter the timing of beacon signal transmission relative to cardiac and/or respiratory motion.

In some examples, the beacon signal 412, the acknowledgment receiving period 414 and/or beacon control interval 409 may be controlled according to different schedules during different time periods or times of day. For example, when the receiving device is configured to schedule beacon search periods 420 at different average polling frequencies according to different polling schedules applied during different time periods, e.g., during the day and during the night as described above, the transmitting device may anticipate longer wait times for the receiving device to detect the beacon signal and transmit the acknowledgment signal 444. As such, the transmitter 90 may be controlled to transmit the beacon signal 412 for a longer time interval, hold the acknowledgment receiving period 414 open for a longer time interval, and or wait for longer beacon control intervals 410 between transmitting repeated beacon signals 412 during the wakeup mode 410 during a first time period than during a second time period, e.g., during the day vs. during the night or vice versa. The beacon signal duration, receiving period 414, and beacon control interval 409 may be controlled according to two or more different schedules based on the time of day to correspond to a polling interval schedule applied by the receiving device during the same time of day.

Upon detection of the acknowledgement signal 444 during the receiving period 414, an acknowledgement detect signal 416 may be generated by the TCC receiver 87 and passed to the control circuit 80 of the transmitting device. The control circuit 80 switches TCC transmitter 90 to the data transmission mode 411 to begin transmitting data packets 430. The TCC transmitter 90 is controlled by controller 91 to generate BPSK modulated data packets during data transmission mode 411. Controller 91 is configured to control drive signal circuit 92 and/or polarity switching circuit 94 to generate FSK modulated signals (as beacon signals) during wakeup mode 410 and configured to control drive signal circuit 92 and/or polarity switching circuit 94 to generate BPSK modulated signals (as datagrams or packets) during data transmission mode 411.

FIG. 11 is a diagram of a data packet 430 that may be transmitted during the data transmission mode 411 of the transmitting device according to one example. Data packet 430 may include multiple fields 490, 492 and 494 transmitted using a carrier signal and BPSK modulation. Thus, the property of the carrier signal being modulated in this case is the phase. A synchronization field 490 is transmitted as the first field at the unmodulated carrier signal frequency, e.g., 100 kHz, to provide a carrier lock for the demodulation by the TCC signal detector 175 of the receiving device, e.g., pacemaker 100 or pressure sensor 50. The synchronization field 490 may include a predetermined number of carrier frequency cycles or bits, e.g., with eight cycles per bit. The synchronization field 490 may be between 128 and 256 cycles long in some examples. In other examples, the synchronization field 490 may be longer to ensure that subsequent fields 492 and 494 including encoded data are transmitted after the AC coupling capacitor 96 is charged to the DC operating voltage prior to encoded data transmission.

The carrier signal transmitted during the synchronization field 490 is modulated during the preamble and data fields 492 and 494 according to a binary coded input signal, which may be produced by a modulator included in controller 91. The preamble field 492 may follow the synchronization field 490 and may be encoded to communicate the type of packet being transmitted and the packet length, e.g. the number of data fields 494. The preamble field 492 may also include a key code to provide bit sample timing to the receiving device, an acknowledgment request bit, source and/or destination address bits, or other bits or bytes that may normally be included in a header or preamble field 492.

Data fields 494 include the information being communicated to the receiving device, which may include commands to perform therapy delivery or signal acquisition, requests for data, control parameter settings to be used by the receiving device for sensing physiological signals and/or delivering a therapy, or numerous other types of information that enable coordination of the IMD system in monitoring the patient and delivering therapy. Each preamble field 492 and data field 494 may include a predetermined number of bytes, e.g., 1 to 254 bytes. Each byte may be a predetermined number of bits, e.g., 8 bits or 13 bits.

FIG. 12 is a conceptual diagram of a portion of one data byte 500 that may be included in a preamble field 492 or a data field 494 of packet 430. Each data byte 500 may be transmitted as the carrier signal 501 modulated using BPSK. The carrier signal 501 has a peak-to-peak amplitude 502 and carrier frequency that is defined by the carrier frequency cycle length 504. The carrier signal 501 has a positive polarity at half the peak-to-peak amplitude 502 during one half of the carrier frequency cycle length 504 and negative polarity at half the peak-to-peak amplitude 502 during the other half of the carrier frequency cycle length 504.

An input digital signal 520 may be generated by transmitter controller 91 to control drive signal circuit 92 and/or polarity switching circuit 94 of transmitter 90 (all shown in FIG. 6) to control modulation of the carrier signal 501 during transmission of data byte 500. Each bit 505-509 of the transmitted TCC signal data byte 500 is encoded by delivering a predetermined number of carrier frequency cycles having a phase that is controlled according to input digital signal 520. In the example shown, each bit 505-509 includes eight carrier frequency cycles 504. The bit value is encoded by controlling drive signal circuit 92 and/or polarity switching circuit 94 to produce either a zero phase shift between bits or a phase shift between bits. No phase shift may correspond to a digital "0" in the bit stream, and a phase shift may correspond to a digital "1" in the bit stream.

To illustrate, the first bit 505 may be a digital "0" and is followed by a phase shift 510 leading into the next bit 506. The phase shift is a positive 180 degrees in this example, but other phase shifts, between ±360 degrees may be used. The TCC signal detector 175 of the receiving device that is locked into the frequency of the carrier signal 501 is configured to detect the phase shift 510. In response to detecting the phase shift 510, the TCC signal detector outputs a digital "1" in digital output signal 524 that is passed to the control circuit of the receiving device for decoding. Bit 506 is followed by no phase shift 512 according to the digital input signal 520 which changes from a digital "1" to a digital "0." The TCC signal detector 175 of the receiving device detects no phase shift and produces a digital "0" for bit 507 in response to detecting no phase shift after the eight cycles of bit 506.

The next bit 507 is followed by a 180 degree positive phase shift 514 in accordance with the change from a digital "0" to a digital "1" in the input digital signal 520. The phase shift 514 is detected by the TCC signal detector 175 and the bit value in the output digital signal 524 changes from "0" to "1" for bit 508. The eight cycles of bit 508 are followed by no phase shift 516, in accordance with a change from "1" to "0" in the input signal 524. In response to no phase shift detection, the TCC signal detector 175 produces a digital "0" in the output digital signal 524 corresponding to the last bit 509. The last five bits of data byte 500 are represented in FIG. 12, however it is recognized that data byte 500 may include 2, 4, 8, 16, or other predetermined number of bits. The last four bits 506-509 may represent a nibble (four bits) of byte 500 including at least 8 bits (an octet) in a hexadecimal encoding scheme. As can be seen in FIG. 12, the encoded data is transmitted during a data packet by continuously transmitting the carrier signal without interruption while controlling the drive signal circuit 92 and the polarity switching circuit 94 to shift the phase of the carrier signal.

Referring again to FIG. 11, the preamble field 492 may include one to four bytes in some examples to provide various header information such as type of data being transmitted, addressing information, number of data fields 494 included in the data packet 430 or other information represented, for example, by one to two bytes each. Each data field 494 may include one byte represented by a stream of eight digital values and each data packet 430 may include 1 to 256 data fields or bytes. In some examples, the data packet 430 may be terminated with a cyclic redundancy check (CRC) field to enable the receiving device to perform an error check. While a particular example of a data packet 430 (or datagram) is shown in FIG. 11, numerous data frame structures including various fields may be conceived according to a particular clinical application and IMD system that utilize an FSK modulated beacon signal during a wakeup mode and a BPSK modulated data packet during a data transmission mode as described herein.

Figure 13:
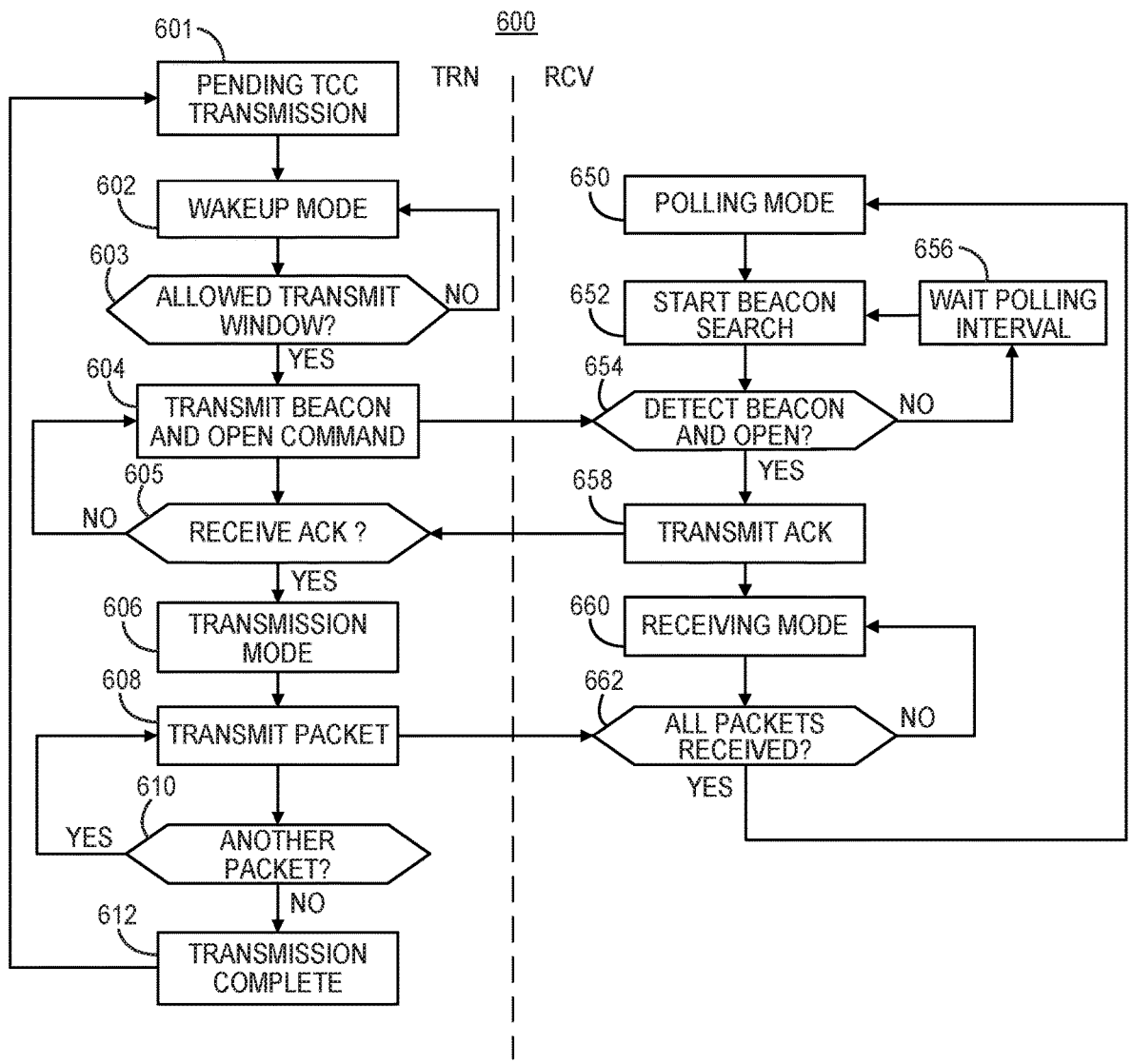
FIG. 13 is a flow chart of a method for transmitting and receiving TCC signals that may be performed by an IMD system according to one example.

FIG. 13 is a flow chart 600 of a method for transmitting and receiving TCC signals that may be performed by an IMD system according to one example. Operations performed by the transmitting device are shown to the left of the vertical dashed line, and operations performed by the receiving device are shown to the right of the horizontal dashed line. The control circuit of the transmitting device, e.g., control circuit 80 of ICD 14 or ICD 214, determines that pending data are ready for TCC transmission at block 601. As described above, the transmitting device may be ICD 14 or ICD 214 operating as a control device initiating the TCC session and the receiving device may be pacemaker 100 or pressure sensor 50 operating as a responder. The receiving device may be a reduced function device with a smaller power supply. For example, the receiving device may be configured to operate in a polling mode to be woken up by another device but may not be configured to operate in a wakeup mode to initiate TCC sessions. It is to be understood, however, that an IMD may be configured to operate as the transmitting device some of the time and operate as the receiving device some of the time and may therefore be configured to operate in a polling mode when not operating in a wakeup mode or transmission mode. For the sake of illustration, the transmitting device is ICD 14 or ICD 214 including transmitter 90 and the receiving device is pacemaker 100 or pressure sensor 50, having a TCC signal detector 175, e.g., as shown in FIG. 3B.

Control circuit 80 powers up transmitter 90 at block 602 to switch transmitter 90 to the wakeup mode from a sleep state, in which power supplied to the circuitry of transmitter 90 is reduced. The controller 91 may control clock circuit 93 to operate according to a low clock frequency that enables generation of the high and low frequencies of the FSK modulated beacon signal. The controller 91 of transmitter 90 may be configured to check whether an allowed transmit window is enabled at block 603. In some examples, control circuit 80 may enable an allowed transmit window signal in response to detecting a cardiac event. A cardiac event may be detected as a sensed cardiac electrical signal generated by the patient's heart and sensed by sensing circuit 86. Additionally, or alternatively, a detected cardiac event may be a pacing pulse or other electrical stimulation pulse generated by therapy circuit 83. The allowed transmit window is described below in conjunction with FIG. 14. If the allowed transmit window is not enabled, the TCC transmitter may wait in the wakeup mode until the allowed transmit window is enabled before transmitting the beacon signal.

At block 604, the beacon signal is transmitted according to any of the examples described above. The beacon signal may be transmitted as an FSK modulated signal having alternating time intervals of high and low frequencies, which may be centered on the carrier signal frequency. The beacon signal may include a distinct end-of-beacon signature that includes a different pattern of one or more time intervals of the high and/or low frequencies than the frequency pattern used prior to the end-of-beacon signature. The beacon signal may be followed by an OPEN command as described above in conjunction with FIG. 10. The transmitting device waits for an acknowledgement signal from the receiving device at block 605 during a receiving window.

If the acknowledgement signal is not received before the receiving window times out, as described in conjunction with FIG. 10, the beacon signal may be re-transmitted by returning to block 604. Alternatively, the transmitting device may wait for an acknowledgement signal after transmitting the beacon signal then transmit the OPEN command in response to receiving the acknowledgement signal. In still other examples, an OPEN command may not be transmitted after the beacon signal. The transmitter 90 may be controlled to transmit the beacon signal, wait for an acknowledgement signal from the receiving device and switch to the data transmission mode.

In response to receiving the acknowledgment signal at block 605, the controller 91 switches the operation of transmitter 90 from the wakeup mode to the data transmission mode at block 606. In other examples, the transmitter 90 may transmit the beacon signal and switch to the data transmission mode without detecting an acknowledgement signal. The transmitter 90 may switch to the data transmission mode after a delay interval to allow the receiving device time to detect the beacon signal and switch from the polling mode to the receiving mode without sending an acknowledgement signal. In some cases, the transmitting device may "know" if transmitted data is successfully received by a receiving device based on the behavior of the receiving device. For example, the transmitting device may be expecting to receive TCC signal data back from the receiving device, e.g., a confirmation signal that data was received or physiological signal data requested by the transmitting device. In other examples, the transmitting device may request therapy delivery by the receiving device, e.g., pacing pulse delivery by pacemaker 100. The transmitting device may detect delivered pacing pulses or associated evoked responses by sensing circuit 86. If an expected response by the receiving device is not detected by the transmitting device, the transmitter 90 may be controlled to resend one or more data packets until the respected response by the receiving device is detected, which may include resending the beacon signal before each set of one or more data packets.

The transmitter is controlled to transmit each data packet using BPSK modulation of the carrier signal at block 608. Multiple data packets may be transmitted in a single transmission session. While not shown explicitly in FIG. 13, it is understood that between data packets, the transmitting device alternate to between data transmission and receiving windows under the control of control circuit 80. During the receiving window, e.g., window 350 shown in FIG. 7, the TCC receiver 87 is enabled to detect and demodulate TCC signals requested from and transmitted by the receiving device. In some cases, a return signal from the receiving device is not requested by the transmitting device so that the receiving window may not be required. After all pending data packets of the TCC transmission session are sent, as determined at block 610 (each followed by a receiving window as needed), the transmission session is completed at block 612. Transmitter 90 may be switched back to a low power, sleep state at block 612, until the next pending TCC transmission session.

The receiving device operates in a polling mode at block 650. The receiving device may operate in the polling mode continuously according to a polling interval schedule until a beacon signal is detected. In some examples, two or more different polling interval schedules having different average polling frequencies may be applied during different respective time periods, e.g., day vs. night polling interval schedules. In still other examples, the receiving device may operate according to the polling mode during designated TCC time periods and the TCC signal detector may be powered down in a sleep state during other time periods. For example, the receiving device may operate in the polling mode for a predetermined time interval once per hour, once per four hours, once per eight hours, once per twelve hours, once per 24 hours or according to another predetermined schedule.

During the polling mode, the TCC signal detector 175 is controlled to start a beacon search period at block 652 according to the polling interval schedule. The TCC signal detector 175 may be configured to detect the FSK modulation of the beacon signal and track the beacon signal to search for the end-of-beacon signature in order to positively detect the beacon signal as described above in conjunction with FIG. 10. In response to detecting the beacon signal, the TCC signal detector 175 waits for an OPEN command at block 654. If the beacon signal is not detected or the OPEN command is not received, the receiving device remains in the polling mode by waiting for the next polling interval to expire at block 656. The next beacon search period is started at block 652.

In response to detecting the beacon signal and receiving the OPEN command (if sent), the receiving device may be configured to transmit an acknowledgement signal back to the transmitting device at block 658. After detecting the beacon signal (and acknowledging the OPEN command if sent), the receiving device switches the TCC signal detector 175 to the receiving mode at block 660 for detecting and demodulating the BPSK signal transmitted by transmitter 90.

The receiving device may determine if all data packets are received at block 662, which may be based on preamble information sent with the transmitted data packets. In other examples, the receiving mode may time out at block 662 if no TCC signal has been detected for a maximum time out interval. The receiving device may switch back to the polling mode at block 650, during which TCC signal detector 175 operates in a lower power state than during the receiving mode. While not explicitly shown in FIG. 13, it is to be understood that the receiving device may operate in a transmitting mode after each data packet as needed in order to transmit a requested confirmation or other data back to the transmitting device. Data transmitted back to the transmitting device may be formatted according to the same or similar data frame and BPSK modulation as described in conjunction with FIGS. 11 and 12 used by the transmitting device. In other examples, simplified confirmation signals may be transmitted from the receiving device back to the transmitting device using a predetermined number of carrier signal cycles without including modulation of the carrier signal.

Figure 14:
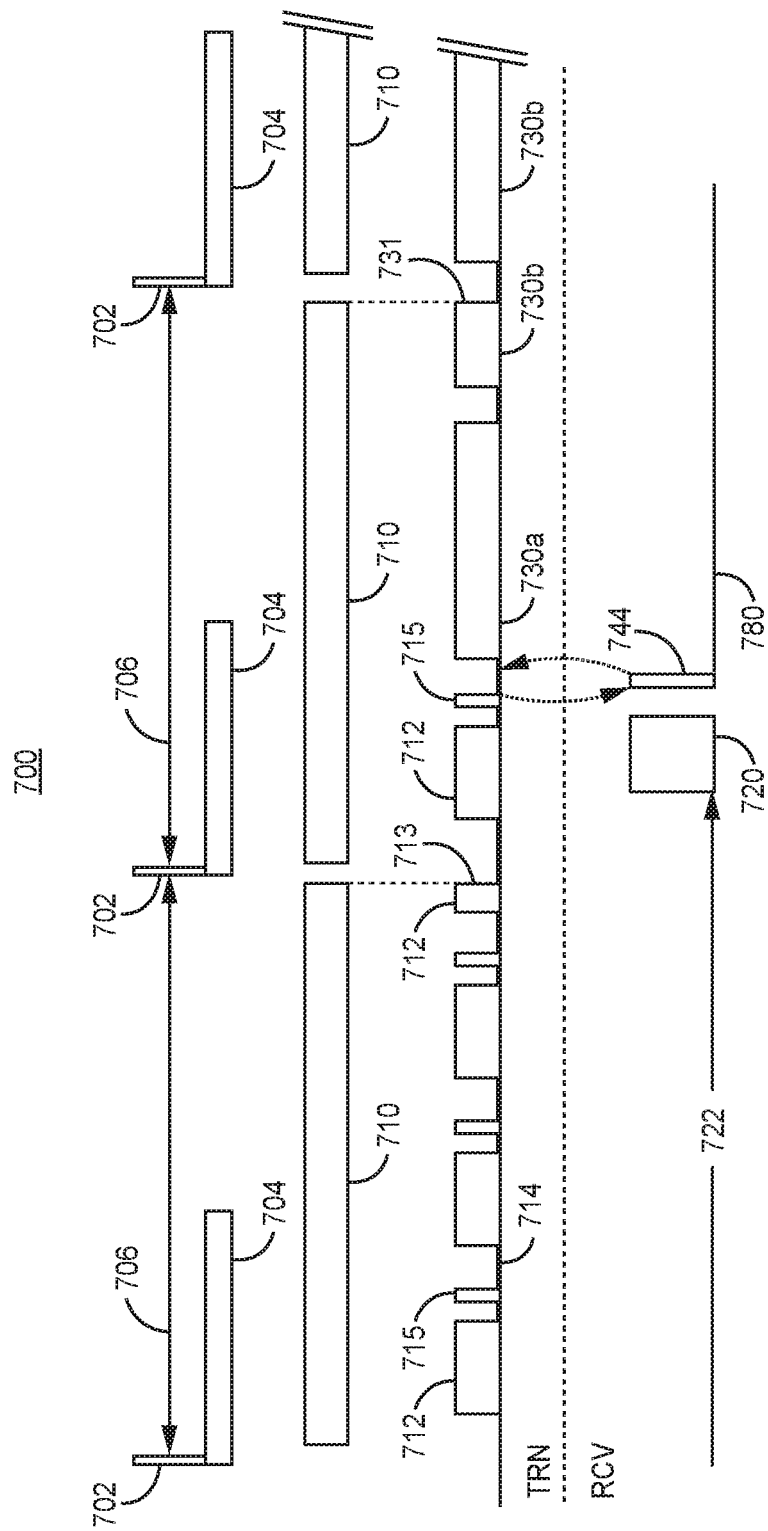
FIG. 14 is a timing diagram of TCC signal transmission control that may be performed by a transmitting IMD according to one example.

FIG. 14 is a timing diagram 700 of TCC signal transmission control that may be performed by a transmitting IMD according to one example. Operations performed by the transmitting device (TRN) are shown above the horizontal dashed line, and operations performed by the receiving device (RCV) are shown below the horizontal dashed line. The control circuit 80 of the transmitting device may be configured to set an allowed transmission window 710 based on the timing of cardiac events 702. The cardiac events 702 may be cardiac pacing pulses or other electrical stimulation pulses generated by therapy circuit 83 at a pacing interval 706. In other examples, cardiac events 702 may be sensed intrinsic cardiac events, e.g., R-waves or P-waves, detected by cardiac event detector 85 at intrinsic cardiac event intervals 706. In still other examples, cardiac events 702 may be pacing pulses delivered by another co-implanted device, such as pacemaker 100, which are detected by cardiac event detector 85 of ICD 14 or ICD 214.

Control circuit 80 may enable the allowed transmission window 710 in response to a first detected cardiac event 702 and disable the allowed transmission window 710 in response to the next, second detected cardiac event 702. The allowed transmission window 710 is terminated or disabled to avoid transmission of the TCC signal during delivery of an electrical stimulation pulse in some examples. As such, the cardiac events 702 may all be cardiac pacing pulses delivered by therapy circuit 83. A pending or ongoing TCC signal may be delayed or halted if the allowed transmission window 710 is not enabled. In some examples, the allowed transmission window 710 may remain enabled if an intrinsic cardiac event is sensed during the allowed transmission window 710. In this case, only electrical stimulation pulses delivered by therapy circuit 83 cause the allowed transmission window 710 to be disabled.

If the control circuit 80 detects a pending TCC signal transmission, the TCC transmitter 90 may be switched from a sleep state to the wakeup mode by controller 91 in response to a control signal from control circuit 80. If the allowed transmission window 710 is not enabled, the controller 91 controls TCC transmitter 90 to wait until the allowed transmission window 710 is set (or enabled) before transmitting the first beacon signal 712. The TCC transmitter 90 may be controlled to transmit multiple beacon signals 712 each followed by an OPEN command 715 and acknowledgment receiving period 714 within an allowed transmission window 710. The allowed transmission window 710 may have a variable time duration since the cardiac event time interval 706 may vary. As such, the TCC transmitter 90 may be in the process of transmitting a beacon signal 712 at the time that the allowed transmission window 710 is terminated. The beacon signal 712 may be halted at 713 in response to the allowed transmission window 710 being disabled. A failed transmission flag may be set so that any halted transmission may be restarted during the next allowed transmission window 710.

The TCC transmitter 90 is controlled by controller 91 to wait for the next allowed transmission window 710 to begin a new beacon signal 712 followed by the OPEN command 715. During the second allowed transmission window 710 shown in FIG. 14, the polling interval 722 of the receiving device TCC signal detector 175 expires, and a beacon search period 720 is started. The receiving device detects the beacon signal 712 and responds to the open command 715 by returning an acknowledgement signal 744 and switching from the polling mode to the receiving mode 780.

The transmitting device switches from the wakeup mode to the data transmission mode in response to receiving the acknowledgement signal 744. If the allowed transmission window 710 is still enabled, the controller 91 of the TCC transmitter 90 controls the drive signal circuit 92 and/or polarity switching circuit 94 to generate and transmitting the first data packet 730*a*. If the data packet is completed without being halted during the allowed transmission window 710, the TCC transmitter 90 may begin transmitting the next data packet 730*b*. The second allowed transmission window 710 is disabled due to the next cardiac event 702. In response to the allowed transmission window 710 being disabled, the next data packet 730*b* is halted at 731. The receiving device may remain in the receiving mode 780 but may generate an error flag based on not receiving a complete data packet and ignore the received bit stream that was halted prematurely. In some examples, the receiving device remains in a receiving mode 780 until a receiving time out window expires without receiving any TCC signal. The controller 91 of transmitter 90 waits to receive an allowed transmission window signal from control circuit 80 then restarts transmission of data packet 730*b*. Data packets may continue to be transmitted at variable intervals between data packets by controlling transmitter 90 to only transmit during allowed transmission windows 710.

In some examples, the TCC transmitter 90 is controlled to start the transmission of the first beacon signal 712 during a blanking period 704, which may be a post-pace blanking period or a post-sense blanking period. An allowed transmission window 710 may be started after delivering a cardiac pacing pulse. If the control circuit 80 determines that a TCC signal transmission is needed during the allowed transmission window 710 but outside a blanking period 704, the control circuit 80 may control the TCC transmitter 90 to wait and start transmitting the first beacon signal 712 during the next automatic post-sense or post-pace blanking period 704. In some examples, only a cardiac pacing pulse or other electrical stimulation pulse delivered by therapy circuit 83 cause the allowed transmission window 710 to be disabled. An intrinsic cardiac event may be sensed during an allowed transmission window 710 without causing the window 710 to be disabled. TCC transmitter 90 may start transmitting the beacon signal 712 during the next blanking period applied to the sensing circuit 86 in response to detecting the intrinsic cardiac event while the allowed transmission window 710 is enabled.

Thus, various examples of a method and apparatus for TCC performed by a medical device system have been presented in the foregoing description with reference to specific embodiments. It is appreciated that various modifications to the referenced embodiments, including combining various aspects of the TCC signal transmission and detection methods in different combinations than the specific combinations described here, may be made without departing from the scope of the disclosure and the following claims. It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single module or circuit for purposes of clarity, it should be understood that the techniques of this disclosure may be performed by a combination of circuits or components associated with, for example, a medical device and/or a single circuit or component may perform multiple functions that are represented as separate circuits or components in the accompanying drawings.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other non-transitory computer-readable medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an IMD system capable of performing TCC has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A device comprising:
   a housing;
   a tissue conduction communication (TCC) transmitter enclosed by the housing and configured to:
   generate a TCC carrier signal having a carrier frequency;
   generate at least one TCC beacon signal by modulating a first property of the TCC carrier signal according to a first type of modulation by:
   modulating the carrier frequency of the TCC carrier signal between a first frequency transmitted for a first number of cycles and a second frequency transmitted for a second number of cycles; and
   terminating the TCC beacon signal with an end-of-beacon signature comprising at least one of the first frequency transmitted for a third number of cycles different than the first number of cycles and/or the second frequency transmitted for a fourth number of cycles different than the second number of cycles;
   generate at least one TCC data signal subsequent to the at least one TCC beacon signal by modulating a second property of the TCC carrier signal different than the first property according to a second type of modulation different than the first type of modulation; and
   transmit the at least one TCC beacon signal and at least one TCC data signal.

2. The device of claim 1, wherein the TCC transmitter is configured to:
   modulate the first property of the TCC carrier signal by modulating the carrier frequency of the TCC carrier signal according to a frequency shift keying (FSK) modulation, and
   modulate the second property of the TCC carrier signal by modulating a phase of the TCC carrier signal according to a phase shift keying (PSK) modulation.

3. The device of claim 1, wherein the TCC transmitter is configured to generate the TCC beacon signal by:
   modulating the carrier frequency of the TCC carrier signal between the first frequency and the second frequency,
   wherein the first frequency is greater than the carrier frequency of the TCC carrier signal and the second frequency is less than the carrier frequency of the TCC carrier signal.

4. The device of claim 1, further comprising:
   a sensing circuit configured to obtain a cardiac electrical signal obtained via a sensing electrode vector; and
   a control circuit coupled to sensing circuit and the TCC transmitter and configured to:
   detect a first cardiac event within the cardiac electrical signal,
   start an allowed transmission window in response to detecting the first cardiac event; and
   control the TCC transmitter to generate the TCC beacon signal during the allowed transmission window.

5. The device of claim 4, wherein:
   the control circuit is configured to:
   detect a second cardiac event within the cardiac electrical signal following the first cardiac event, and
   terminate the allowed transmission window in response to detecting the second cardiac event; and
   the TCC transmitter is configured to:
   terminate one of the TCC beacon signal and the TCC data signal being transmitted at the termination of the allowed transmission window.

6. The device of claim 5, further comprising a therapy circuit configured to generate and deliver a cardiac electrical stimulation pulse;
   wherein the control circuit is configured to detect the second cardiac event in response to the generated electrical stimulation pulse.

7. The device of claim 4, wherein the control circuit is configured to apply a blanking period to the sensing circuit in response to detecting the first cardiac event;

wherein TCC transmitter is configured to start generating the TCC beacon signal during the blanking period.

8. The device of claim 1, further comprising a TCC receiver configured to receive an acknowledgment signal during a receiving period subsequent to the TCC beacon signal;

the TCC transmitter being further configured to:
adjust at least one of a TCC beacon signal duration, the receiving period, and/or a beacon control interval in response to the receiving period expiring without the TCC receiver receiving the acknowledgment signal; and
control the TCC transmitter to generate a next TCC beacon signal after the beacon control interval in response to the TCC receiver not receiving the acknowledgment signal during the receiving period.

9. The device of claim 1, wherein the TCC transmitter is further configured to:
adjust at least one of a TCC beacon signal duration, an acknowledgment receiving period, and/or a beacon control interval based on a time of day.

10. The device of claim 1, wherein the TCC transmitter is configured to generate the TCC beacon signal having a first peak-to-peak amplitude that is not modulated during the TCC beacon signal and generate the TCC data signal having a second peak-to-peak amplitude that is not modulated during the TCC data signal, the first peak-to-peak amplitude being greater than the second peak-to-peak amplitude.

11. The device of claim 1, further comprising:
a clock circuit configured to generate a first clock signal having a first clock frequency and generate a second clock signal having a second clock frequency greater than the first clock frequency,
wherein the TCC transmitter is configured to:
generate the TCC carrier signal at the carrier frequency using the first clock signal for generating the at least one beacon signal; and
generate the TCC carrier signal at the carrier frequency using the second clock frequency greater than the first clock frequency for generating the at least one TCC data signal.

12. A method comprising:
generating a tissue conduction communication (TCC) carrier signal having a carrier frequency;
generating at least one TCC beacon signal by modulating a first property of the TCC carrier signal according to a first type of modulation by modulating the carrier frequency of the TCC carrier signal between a first frequency transmitted for a first number of cycles and a second frequency transmitted for a second number of cycles; and
terminating the TCC beacon signal with an end-of-beacon signature comprising at least one of the first frequency transmitted for a third number of cycles different than the first number of cycles and/or the second frequency transmitted for a fourth number of cycles different than the second number of cycles; and
generating a TCC data signal subsequent to the TCC beacon signal by modulating a second property of the TCC carrier signal different than the first property according to a second type of modulation different than the first type of modulation.

13. The method of claim 12, wherein:
modulating the first property of the TCC carrier signal comprises modulating the carrier frequency of the TCC carrier signal according to a frequency shift keying (FSK) modulation, and
modulating the second property of the TCC carrier signal comprises modulating a phase of the TCC carrier signal according to a phase shift keying (PSK) modulation.

14. The method of claim 12, wherein generating the TCC beacon signal comprises:
modulating the carrier frequency of the TCC carrier signal between the first frequency,
wherein the first frequency is greater than the carrier frequency of the TCC carrier signal and the second frequency is less than the carrier frequency of the TCC carrier signal.

15. The method of claim 12, further comprising:
detecting a first cardiac event within a cardiac electrical signal;
starting an allowed transmission window by the control circuit in response to detecting the first cardiac event; and
controlling the TCC transmitter to generate the TCC beacon signal during the allowed transmission window.

16. The method of claim 15, further comprising:
detecting a second cardiac event within the cardiac electrical signal following the first cardiac event by the control circuit;
terminating the allowed transmission window in response to detecting the second cardiac event; and
terminating one of the TCC beacon signal and the TCC data signal being transmitted at the termination of the allowed transmission window.

17. The method of claim 16, further comprising:
delivering an electrical stimulation pulse; and
detecting the second cardiac event in response to the generated electrical stimulation pulse.

18. The method of claim 15, further comprising:
applying a blanking period to a sensing circuit that is configured to receive the cardiac electrical signal, the blanking period applied in response to detecting the first cardiac event; and
starting generation of the TCC beacon signal during the blanking period.

19. The method of claim 12, further comprising:
enabling a TCC receiver for a receiving period subsequent to generating the TCC beacon signal;
adjusting at least one of a TCC beacon signal duration, the receiving period, and/or a beacon control interval in response to the receiving period expiring without the TCC receiver receiving an acknowledgment signal; and
controlling the TCC transmitter to generate a next TCC beacon signal after the beacon control interval in response to the TCC receiver not receiving the acknowledgment signal during the receiving period.

20. The method of claim 12, further comprising adjusting at least one of a TCC beacon signal duration, an acknowledgment receiving period, and/or a beacon control interval based on a time of day.

21. The method of claim 12, further comprising wherein generating the TCC beacon signal comprises generating the TCC beacon signal having a first peak-to-peak amplitude that is not modulated during the TCC beacon signal and generate the TCC data signal having a second peak-to-peak amplitude that is modulated during the TCC data signal, the first peak-to-peak amplitude being greater than the second peak-to-peak amplitude.

22. The method of claim 12, wherein:
generating the TCC beacon signal comprises controlling a clock circuit to generate a first clock signal having a first clock frequency to generate the TCC carrier signal at the carrier frequency; and
generating the TCC data signal comprises controlling the clock circuit to generate a second clock signal having a second clock frequency to generate the TCC carrier signal at the carrier frequency, the second clock frequency greater than the first clock frequency.

23. A device comprising:
a housing;
a tissue conduction communication (TCC) transmitter enclosed by the housing and configured to:
generate a TCC carrier signal;
generate at least one TCC beacon signal by modulating a first property of the TCC carrier signal according to a first type of modulation by:
  modulating a frequency of the TCC carrier signal a plurality of times between a first frequency transmitted for a first fixed number of cycles and a second frequency transmitted for a second fixed number of cycles, and
  terminating the TCC beacon signal with an end-of-beacon signature to enable a receiving device to positively detect the end of the beacon signal, the end-of-beacon signature comprising at least one of the first frequency transmitted for a distinct third number of cycles greater than the first fixed number of cycles and/or the second frequency transmitted for a distinct fourth number of cycles greater than the second fixed number of cycles;
generate at least one TCC data signal subsequent to the at least one TCC beacon signal by modulating the TCC carrier signal according to a second type of modulation different than the first type of modulation; and
transmit the at least one TCC beacon signal and at least one TCC data signal.

\* \* \* \* \*